(12) United States Patent
Ie et al.

(10) Patent No.: US 7,932,347 B2
(45) Date of Patent: Apr. 26, 2011

(54) POLYMER COMPRISING UNIT COMPRISING FLUOROCYCLOPENTANE RING FUSED WITH AROMATIC RING AND ORGANIC THIN FILM AND ORGANIC THIN FILM ELEMENT BOTH COMPRISING THE SAME

(75) Inventors: Yutaka Ie, Suita (JP); Yoshio Aso, Suita (JP); Yoshikazu Umemoto, Suita (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 219 days.

(21) Appl. No.: 12/066,006

(22) PCT Filed: Aug. 28, 2006

(86) PCT No.: PCT/JP2006/316901
§ 371 (c)(1),
(2), (4) Date: May 1, 2008

(87) PCT Pub. No.: WO2007/029547
PCT Pub. Date: Mar. 15, 2007

(65) Prior Publication Data
US 2008/0302419 A1     Dec. 11, 2008

(30) Foreign Application Priority Data

Sep. 8, 2005   (JP) .............................. P2005-261284
Mar. 10, 2006  (JP) .............................. P2006-066729

(51) Int. Cl.
*C08G 75/00* (2006.01)
(52) U.S. Cl. ........ 528/373; 528/380; 528/377; 136/263; 428/220; 257/40; 257/E31; 257/E51
(58) Field of Classification Search ............... 528/373, 528/380; 136/263; 428/220; 257/40, E31, 257/E5
See application file for complete search history.

(56) References Cited

U.S. PATENT DOCUMENTS

2002/0060321 A1* 5/2002 Kazlas et al. .................. 257/66
2004/0183068 A1   9/2004 Ong et al.
2004/0186266 A1   9/2004 Jiang et al.

FOREIGN PATENT DOCUMENTS

EP        1 279 689 A2    1/2003
(Continued)

OTHER PUBLICATIONS

Uchida et al. (Advanced Materials, 15, 10, May 16, 2003, p. 785-788).*
T. Izumi et al., "Synthesis and Spectroscopic properties of a Series of Beta-Blocked Long Oligothiophenes up to the 96-mer: Revaluation of Effective Conjugation Length", J. Am. Chem. Soc., (2003), 125, pp. 5286-5287.

(Continued)

*Primary Examiner* — Randy Gulakowski
*Assistant Examiner* — Shane Fang
(74) *Attorney, Agent, or Firm* — Sughrue Mion, PLLC

(57) ABSTRACT

A polymer comprising a repeating unit represented by the following general formula (I). (In the formula, $Ar^1$ represents a divalent aromatic hydrocarbon or divalent heterocyclic group, $X^1$, $Y^1$, $X^2$ and $Y^2$ each independently represent a fluorine atom or alkylthio group, and $X^1$ and $Y^1$ and $X^2$ and $Y^2$ may together form a carbonyl or thiocarbonyl group with their bonding carbon atom.)

(I)

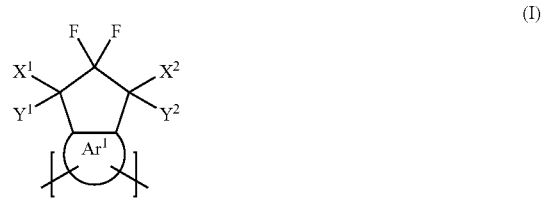

19 Claims, 12 Drawing Sheets

FOREIGN PATENT DOCUMENTS

| | | |
|---|---|---|
| JP | 2-202514 A | 8/1990 |
| JP | 05021824 * | 1/1993 |
| JP | 5-110069 A | 4/1993 |
| JP | 2003-176338 A | 6/2003 |
| JP | 2003-192772 A | 7/2003 |
| JP | 2004-6476 | 1/2004 |
| WO | 03/010778 A1 | 2/2003 |
| WO | WO 2004/031192 A1 | 4/2004 |

OTHER PUBLICATIONS

Y. Ie et al., "Synthesis and Properties of Hexafluorocyclopenta[c]thiophene-based Oligothiophenes", The Institute of Scientific and Industrial Research, Osaka University, (Aug. 29, 2005).

* cited by examiner

POLYMER COMPRISING UNIT COMPRISING FLUOROCYCLOPENTANE RING FUSED WITH AROMATIC RING AND ORGANIC THIN FILM AND ORGANIC THIN FILM ELEMENT BOTH COMPRISING THE SAME

TECHNICAL FIELD

The present invention relates to polymers containing fused units of fluorinated cyclopentane rings and aromatic rings, and to organic thin-films and organic thin-film elements employing them.

BACKGROUND ART

Thin-films containing organic materials with electron transport or hole transport properties have many potential applications in organic thin-film elements such as organic thin-film transistors, organic solar cells, optical sensors and the like, but because organic n-type semiconductors (that exhibit electron transport properties) are harder to obtain than organic p-type semiconductors (that exhibit hole transport properties), a great deal of research effort is being expended on developing organic n-type semiconductors.

Because fluoroalkyl group-introduced π-conjugated compounds have increased electron acceptability, such compounds can potentially be developed into electron transport materials such as organic n-type semiconductors. Much research has therefore been devoted in recent years to compounds obtained by introducing fluoroalkyl groups into thiophene rings, and particularly oligothiophene rings (Patent documents 1-4).

On the other hand, oligomers with cyclopentane ring-fused thiophenes as base units have greater effective conjugation lengths than oligothiophenes with linear alkyl groups (Non-patent document 1).

[Patent document 1] U.S. Patent Application Publication No. 2004/186266
[Patent document 2] U.S. Patent Application Publication No. 2004/183068
[Patent document 3] International Patent Publication No. 2003/010778
[Patent document 4] European Patent Application Publication No. 1279689
[Non-patent document 1] Izumi, T.; Kobashi, S.; Takimiya, K.; Aso, Y.; Otsubo, T.: J. Am. Chem. Soc. 2003, 125, 5286.

DISCLOSURE OF THE INVENTION

Problems to be Solved by the Invention

The performance of the known oligomers mentioned above as organic n-type semiconductors is less than satisfactory, and organic n-type semiconductors with further improved electron transport properties are desired.

It is therefore an object of the present invention to provide novel polymers that can be used as organic n-type semiconductors with excellent electron transport properties. It is another object of the invention to provide organic thin-films containing the novel polymers and organic thin-film elements comprising the organic thin-films.

Means for Solving the Problems

In order to achieve the object stated above, the invention provides polymers having a repeating unit represented by the following general formula (I).

[Chemical Formula 1]

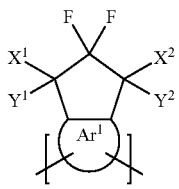

(I)

In the formula, $Ar^1$ represents a divalent aromatic hydrocarbon group or divalent heterocyclic group (which may optionally have substituents), and $X^1$, $Y^1$, $X^2$ and $Y^2$ each independently represent a fluorine atom or alkylthio group (with $X^1$ and $Y^1$ optionally having their alkyl portions linked to form an alkylenedithio group, and $X^2$ and $Y^2$ optionally having their alkyl portions linked to form an alkylenedithio group). Also, $X^1$ and $Y^1$ may together form a carbonyl or thiocarbonyl group with their bonding carbon atom, and $X^2$ and $Y^2$ may together form a carbonyl or thiocarbonyl group with their bonding carbon atom.

A polymer having this type of structural backbone has satisfactory π conjugated planarity between rings, and can therefore be used as an organic n-type semiconductor with highly superior electron transport properties. Such polymers are also chemically stable, have excellent solubility in solvents and exhibit sufficiently low LUMO, and can therefore be used to form thin films for production of organic thin-film elements with excellent performance.

Effect of the Invention

The invention provides novel polymers that can be used as organic n-type semiconductors with excellent electron transport properties. The invention further provides organic thin-films containing the novel polymers and organic thin-film elements comprising the organic thin-films. Among the novel polymers, those with a 3,3,4,4,5,5-hexafluorocyclopenta[c]thiophene structure have a particularly low LUMO level due to introduction of the fluorocyclopentane ring, and their solubility in organic solvents is increased while π conjugated planarity is maintained. The novel polymers are therefore useful as organic n-type semiconductors with notably high electron transport properties. The novel polymers can also be easily obtained by oligomerization or polymerization of starting compounds. The polymers of the invention obtained in this manner are especially useful for production of organic transistors, organic solar cells, optical sensors and the like.

EXPLANATION OF SYMBOLS

Figure 1:
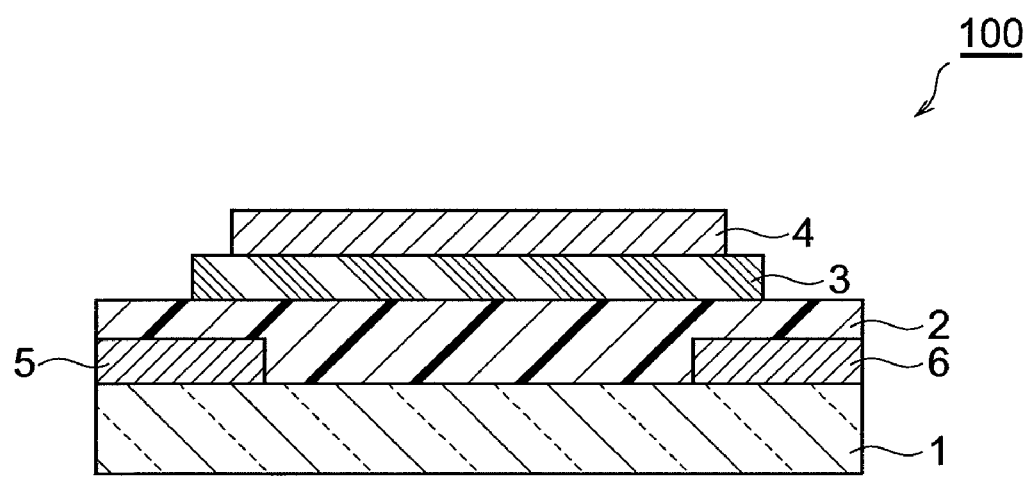
FIG. 1 is a schematic cross-sectional view of an organic thin-film transistor according to a first embodiment.

1: Substrate, 2: active layer, 2a: active layer, 3: insulating layer, 4: gate electrode, 5: source electrode, 6: drain electrode, 7a: first electrode, 7b: second electrode, 8: charge generation layer, 100: first embodiment of organic thin-film transistor, 110: second embodiment of organic thin-film transistor, 120: third embodiment of organic thin-film transistor, 130: fourth embodiment of organic thin-film transistor, 140: fifth embodiment of organic thin-film transistor, 150: sixth embodiment of organic thin-film transistor, 160: seventh embodiment of organic thin-film transistor, 200: embodiment of solar cell, 300: first embodiment of optical sensor, 310: second embodiment of optical sensor, 320: third embodiment of optical sensor.

BEST MODES FOR CARRYING OUT THE INVENTION

Preferred embodiments of the invention will now be explained in detail, with reference to the accompanying drawings as necessary. Identical elements in the drawings will be referred to by like reference numerals and will be explained only once. The vertical and horizontal positional relationships are based on the positional relationships in the drawings, unless otherwise specified. Also, the dimensional proportions depicted in the drawings are not necessarily limitative.

A polymer of the invention has a repeating unit represented by general formula (I) shown above. More specifically, it has at least one, preferably 2 or greater, even more preferably 4 or greater and yet more preferably 6 or greater repeating units represented by general formula (I) (for example, as repeating units represented by general formula (II) shown below), and may have other repeating units as well. The upper limit for the repeating units represented by general formula (I) in the polymer will normally be about 1000. More than one $X^1$, $Y^1$, $X^2$, $Y^2$ and $Ar^1$ will be present in the polymer, and the $X^1$, $Y^1$, $X^2$, $Y^2$ and $Ar^1$ may be identical or different in each group. In order to facilitate production, the multiple $X^1$, $Y^1$, $X^2$, $Y^2$ and $Ar^1$ are preferably identical in each group.

In general formula (I), $Ar^1$ represents a divalent aromatic hydrocarbon group or divalent heterocyclic group, which may have one or more optional substituents, and $X^1$, $Y^1$, $X^2$ and $Y^2$ each independently represent fluorine or an alkylsulfanyl group (alkylthio group) (examples of which are shown in the following general formulas (Ia) and (Ib), where the $R^{10}$ groups are identical or different alkyl groups), or $X^1$ and $Y^1$ together optionally form an alkylenedithio group (—S-$L^1$-S—, where $L^1$ is an alkylene group such as methylene, ethylene, propylene or butylene), or $X^2$ and $Y^2$ together optionally form an alkylenedithio group (—S-$L^2$-S—, where $L^2$ is an alkylene group such as methylene, ethylene, propylene or butylene) (an example of which is shown in the following general formula (Ic)), or $X^1$ and $Y^1$ optionally form a carbonyl group or thiocarbonyl group with their bonding carbon atom, and $X^2$ and $Y^2$ optionally form a carbonyl group or thiocarbonyl group with their bonding carbon atom (examples of which are shown in the following general formulas (Id) and (Ie)).

[Chemical Formula 2]

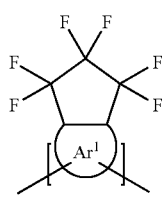

(Ia)

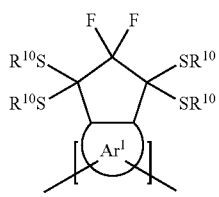

(Ib)

[Chemical Formula 3]

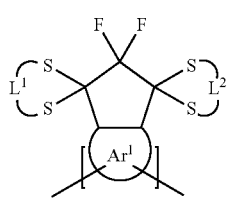

(Ic)

[Chemical Formula 4]

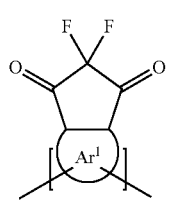

(Id)

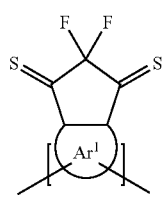

(Ie)

The repeating unit represented by general formula (I) above is preferably a repeating unit represented by the following general formula (II), in which case the repeating units corresponding to general formulas (Ia), (Ib), (Ic), (Id) and (Ie) will be ones corresponding to the following general formulas (IIa), (IIb), (IIc), (IId) and (IIe).

[Chemical Formula 5]

(II)
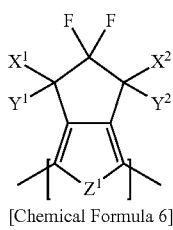

[Chemical Formula 6]

(IIa)
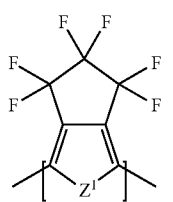

(IIb)
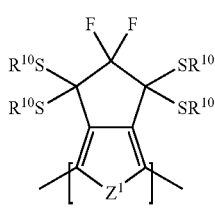

[Chemical Formula 7]

(IIc)
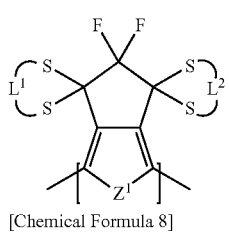

[Chemical Formula 8]

(IId)
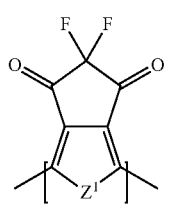

(IIe)
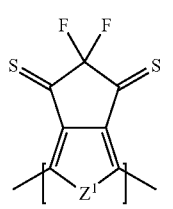

The polymer may have in the molecule any one of the repeating units represented by general formulas (Ia), (Ib), (Ic), (Id) and (Ie) or general formulas (IIa), (IIb), (IIc), (IId) and (IIe), or it may have more than one of different repeating units. For facilitated production, it preferably has only one of the repeating units, in which case the repeating unit of general formula (Ia) or (IIa) is preferred.

In the general formulas (II), (IIa), (IIb), (IIc), (IId) and (IIe), $Z^1$ may be a group represented by any of the following formulas (i)-(ix). $R^1$, $R^2$, $R^3$ and $R^4$ each independently represent hydrogen or a substituent, and a ring may be formed between $R^2$ and $R^3$. The group represented by the following formula (ix) may be left-right inverted.

[Chemical Formula 9]

 (i)

 (ii)

 (iii)

 (iv)

 (v)

 (vi)

 (vii)

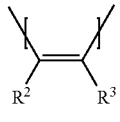 (viii)

(xix)

The polymer of the invention preferably comprises at least one repeating unit represented by general formula (I) and at least one repeating unit represented by the following general formula (III) which is different from the repeating unit represented by general formula (I). The polymer more preferably comprises at least one repeating unit represented by general formula (II) and at least one repeating unit represented by the following general formula (III) which is different from the repeating unit represented by general formula (I), and even more preferably it comprises at least one repeating unit represented by general formula (II) and at least one repeating unit represented by the following general formula (IV). Such a structure will widen the range of variability for the soluble, mechanical, thermal and electronic characteristics. From the viewpoint of increasing the solubility in organic solvents, a substituent is preferably included in general formula (III) or general formula (IV). The substituent is preferably a C3-20 long-chain alkyl or C3-20 long-chain alkoxy group. The long-chain alkyl or long-chain alkoxy group may be branched. $Ar^2$ in the formula represents a divalent aromatic hydrocarbon or divalent heterocyclic group (which may be optionally substituted). The ratio of the repeating unit represented by general formula (I) and the repeating unit represented by general formula (III) is preferably 10-1000 mol of the latter to 100 mol of the former, more preferably 25-400 mol of the latter to 100 mol of the former and even more preferably 50-200 mol of the latter to 100 mol of the former.

[Chemical Formula 10]

(III)

Here, $Ar^2$ is preferably a group represented by the following formula (IV). In this formula, $Z^2$ is the same as or different from $Z^1$, and is a group from among those represented by formulas (i)-(ix) above. $R^5$ and $R^6$ each independently represent hydrogen or a substituent, and a ring may be formed between $R^5$ and $R^6$. $R^1$, $R^2$, $R^3$ and $R^4$ are the same as defined above.

[Chemical Formula 11]

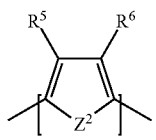
(IV)

In the general formulas shown above, the divalent aromatic hydrocarbon groups represented by $Ar^1$ and $Ar^2$ may be groups remaining after removing two hydrogen atoms from a benzene ring or fused ring, and the number of carbon atoms will generally have 6-60 and preferably 6-20 carbon atoms. As examples of fused rings there may be mentioned naphthalene, anthracene, pyrene, perylene and fluorene. Preferred among these are atomic groups remaining after removing two hydrogen atoms from a benzene ring or fluorene. The aromatic hydrocarbon groups may be optionally substituted. The number of carbon atoms of the substituents are not included in the number of carbon atoms in the divalent aromatic hydrocarbon groups. As substituents there may be mentioned halogen atoms and saturated or unsaturated hydrocarbon, aryl, alkoxy, arylalkyl, aryloxy, heterocyclic, amino, nitro and cyano groups.

The divalent heterocyclic groups represented by $Ar^1$ or $Ar^2$ may also be atomic groups remaining after removing two hydrogen atoms from a heterocyclic compound, where the number of carbon atoms will normally be 4-60 and preferably 4-20. The heterocyclic groups may have substituents, in which case the numbers of carbon atoms of the substituents are not included in the numbers of carbon atoms of the heterocyclic groups. As substituents there may be mentioned halogen atoms and saturated or unsaturated hydrocarbon, aryl, alkoxy, arylalkyl, aryloxy, heterocyclic, amino, nitro and cyano groups.

A heterocyclic compound referred to here is an organic compound with a ring structure wherein the elements composing the ring include not only carbon but also heteroatoms such as oxygen, sulfur, nitrogen, phosphorus, boron and silicon in the ring.

The arrangement of the repeating units is preferably such that a repeating unit represented by general formula (III) or (IV) is adjacent to a repeating unit represented by general formula (I) or (II), and more preferably such that a repeating unit represented by general formula (III) or (IV) is adjacent to a repeating unit represented by general formula (I) or (II) on both sides. A structure wherein repeating units represented by general formula (I) and (II) are alternating is also preferred. When a repeating unit represented by general formula (IV) is adjacent to a repeating unit represented by general formula (I) or (II), there are preferably no substituents on the carbon in the ring containing $Z^2$ of the repeating unit represented by general formula (IV), which is adjacent to the carbon atom bonded to the adjacent repeating unit represented by general formula (I) or (II). The ring containing $Z^2$ of the repeating unit represented by general formula (IV) is preferably a 5-membered ring.

The polymers of the invention are expected to have high electron transport properties as organic n-type semiconductors. Electron-withdrawing groups are preferred as substituents in order to increase the effect, since they lower the LUMO level as well. From this viewpoint, it is important for the units represented by general formula (I) and (II) to contain fluorine atoms. In order to further lower the LUMO level and increase the electron transport property, at least one from among $X^1$, $Y^1$, $X^2$ and $Y^2$ is preferably an electron-withdrawing group. Polymers wherein all of $X^1$, $Y^1$, $X^2$ and $Y^2$ are fluorine atoms are more preferred, and are suitable as thin-film materials for organic thin-film elements with organic n-type semiconductors. An oligomer or polymer containing a thiophene structure not only can lower the LUMO level by introduction of the hexafluorocyclopentane ring, but can also increase the solubility in organic solvents and help to improve performance as an organic semiconductor and lower production cost, since π conjugated planarity is maintained. An organic thin-film element of the invention exhibits high performance by containing an oligomer or polymer of the invention which contains the aforementioned hexafluorocyclopentane ring.

$Z^1$ in general formula (II) and $Z^2$ in general formula (IV) are each preferably a group represented by any of formulas (i), (ii), (iii), (viii) and (ix) above, more preferably a group represented by any of formulas (i), (ii) and (iii) above, and most preferably a group represented by formula (i). Thiophene rings, furan rings and pyrrole rings, and especially thiophene rings, exhibit characteristic electrical properties, and their fusion with hexafluorocyclopentane rings can result in new electrical properties that are non-existent in the prior art.

In formulas (iii), (viii) and (ix) and general formula (IV), $R^1$-$R^6$ each independently represent hydrogen or a substituent, and $R^2$ and $R^3$ or $R^5$ and $R^6$ may form a ring.

Preferably, $R^1$-$R^6$ each independently represent hydrogen, a halogen atom, a straight-chain or branched low molecular chain, a monovalent cyclic group (which may be a monocycle or fused ring, a carbon ring or heterocyclic ring, saturated or unsaturated, and with or without substituents), or an electron-donating or electron-withdrawing group.

More preferably, $R^1$-$R^6$ each independently represent hydrogen, a halogen atom, a straight-chain or branched low molecular chain, a C3-60 monovalent cyclic group (which may be a monocycle or fused ring, a carbon ring or heterocyclic ring, saturated or unsaturated, and with or without substituents), a saturated or unsaturated hydrocarbon group, hydroxyl, alkoxy, alkanoyloxy, amino, oxyamino, alkylamino, dialkylamino, alkanoylamino, cyano, nitro, sulfo, alkyl optionally substituted with one or more halogen atoms, alkoxysulfonyl (where the alkyl group is optionally substituted with one or more halogen atoms), alkylsulfonyl (where the alkyl group is optionally substituted with one or more halogen atoms), sulfamoyl, alkylsulfamoyl, carboxyl, carbamoyl, alkylcarbamoyl, alkanoyl or alkoxycarbonyl.

According to the invention, "halogen atoms" includes all of the halogens, and fluorine, chlorine, bromine and iodine may be mentioned as examples.

There are no restrictions on the alkyl groups, for which methyl, ethyl, n-propyl, isopropyl, n-butyl, isobutyl, sec-butyl and tert-butyl may be mentioned as examples, and this also applies for groups containing alkyl groups in their structures (such as alkoxy, alkylamino group and alkoxycarbonyl).

The unsaturated hydrocarbon groups are not restricted, and vinyl, 1-propenyl, allyl, propargyl, isopropenyl, 1-butenyl and 2-butenyl may be mentioned as examples.

There are no particular restrictions on alkanoyl groups, of which formyl, acetyl, propionyl, isobutyryl, valeryl and isovaleryl may be mentioned as examples, and this also applies for groups containing alkanoyl groups in their structures (such as alkanoyloxy and alkanoylamino). A "C1 alkanoyl group" is formyl, also for groups containing alkanoyl groups in their structures.

Even more preferably, $R^1$-$R^6$ each independently represent hydrogen, a halogen atom, a substituted or unsubstituted, saturated or unsaturated straight-chain or branched hydrocarbon group, hydroxyl, C1-18 straight-chain or branched alkyl, C2-18 straight-chain or branched unsaturated hydrocarbon, C1-18 straight-chain or branched alkoxy, C2-18 straight-chain or branched alkanoyloxy, amino, oxyamino, C1-18 straight-chain or branched alkylamino, dialkylamino (where the alkyl group is a C1-18 straight-chain or branched alkyl group), C1-18 straight-chain or branched alkanoylamino, cyano, nitro, sulfo, C1-18 straight-chain or branched alkyl substituted with one or more halogen atoms, C1-18 straight-chain or branched alkoxysulfonyl (where the alkyl group is optionally substituted with one or more halogen atoms), C1-18 straight-chain or branched alkylsulfonyl (where the alkyl group is optionally substituted with one or more halogen atoms), sulfamoyl, C1-18 straight-chain or branched alkylsulfamoyl, carboxyl, carbamoyl, C1-18 straight-chain or branched alkylcarbamoyl, C1-18 straight-chain or branched alkanoyl or C1-18 straight-chain or branched alkoxycarbonyl.

Yet more preferably, $R^1$-$R^6$ each independently represent hydrogen, a halogen atom, a substituted or unsubstituted, saturated or unsaturated straight-chain or branched hydrocarbon chain, hydroxyl, C1-6 straight-chain or branched alkyl, C2-6 straight-chain or branched unsaturated hydrocarbon, C1-6 straight-chain or branched alkoxy, C2-6 straight-chain or branched alkanoyloxy, amino, oxyamino, C1-6 straight-chain or branched alkylamino, dialkylamino (where the alkyl group is a C1-6 straight-chain or branched alkyl group), C1-6 straight-chain or branched alkanoylamino, cyano, nitro, sulfo, C1-6 straight-chain or branched alkyl substituted with one or more hydrogens, C1-6 straight-chain or branched alkoxysulfonyl (where the alkyl group is optionally substituted with one or more halogen atoms), C1-6 straight-chain or branched alkylsulfonyl (where the alkyl group is optionally substituted with one or more halogen atoms), sulfamoyl, C1-6 straight-chain or branched alkylsulfamoyl, carboxyl, carbamoyl, C1-6 straight-chain or branched alkylcarbamoyl, C1-6 straight-chain or branched alkanoyl or C1-6 straight-chain or branched alkoxycarbonyl.

Preferably, $R^1$-$R^6$ each independently represent hydrogen, a halogen atom, a C1-18 straight-chain hydrocarbon or a monovalent cyclic group having a structure derived by removing any one hydrogen from a compound represented by any of the following formulas (1)-(67) (where the cyclic group may be further substituted with one or more substituents which are each independently selected from among halogen atoms, saturated or unsaturated hydrocarbons, aryl, alkoxy, aryloxy, heterocyclic, amino, nitro and cyano.

[Chemical Formula 12]

(1)

(2)

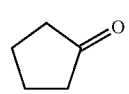

(3)

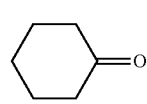

(4)

(5)

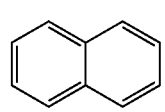

(6)

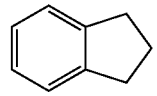

(7)

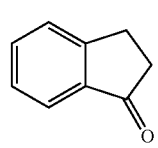

(8)

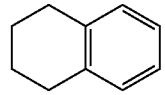

(9)

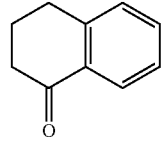

(10)

(11)

(12)

(13)

(14)

-continued
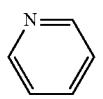 (15)
 (16)
 (17)
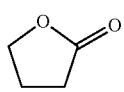 (18)
 (19)
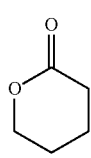 (20)
 (21)
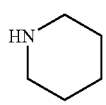 (22)
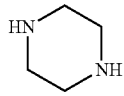 (23)
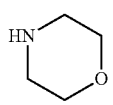 (24)
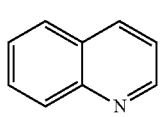 (25)
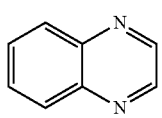 (26)
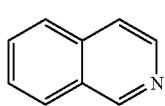 (27)
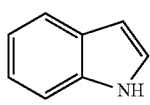 (28)
-continued
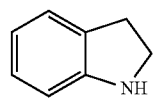 (29)
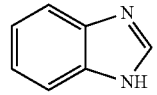 (30)
[Chemical Formula 13]
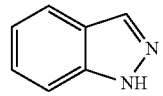 (31)
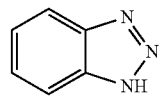 (32)
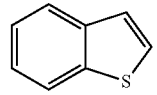 (33)
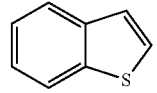 (34)
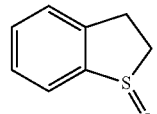 (35)
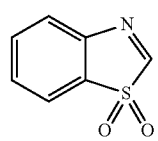 (36)
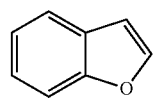 (37)
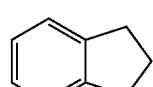 (38)
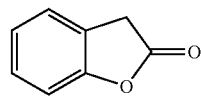 (39)
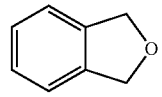 (40)
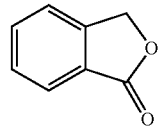 (41)

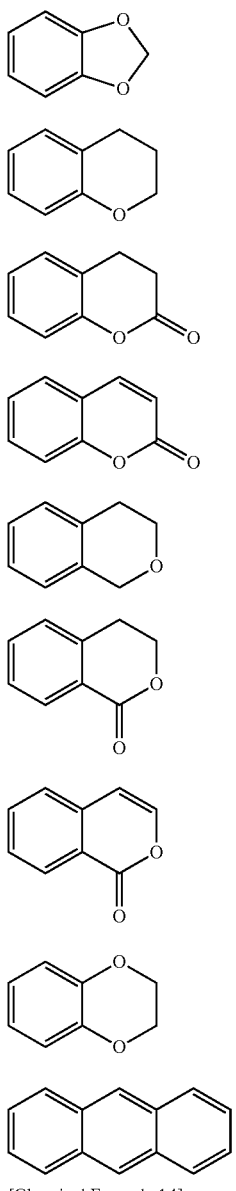
[Chemical Formula 14]
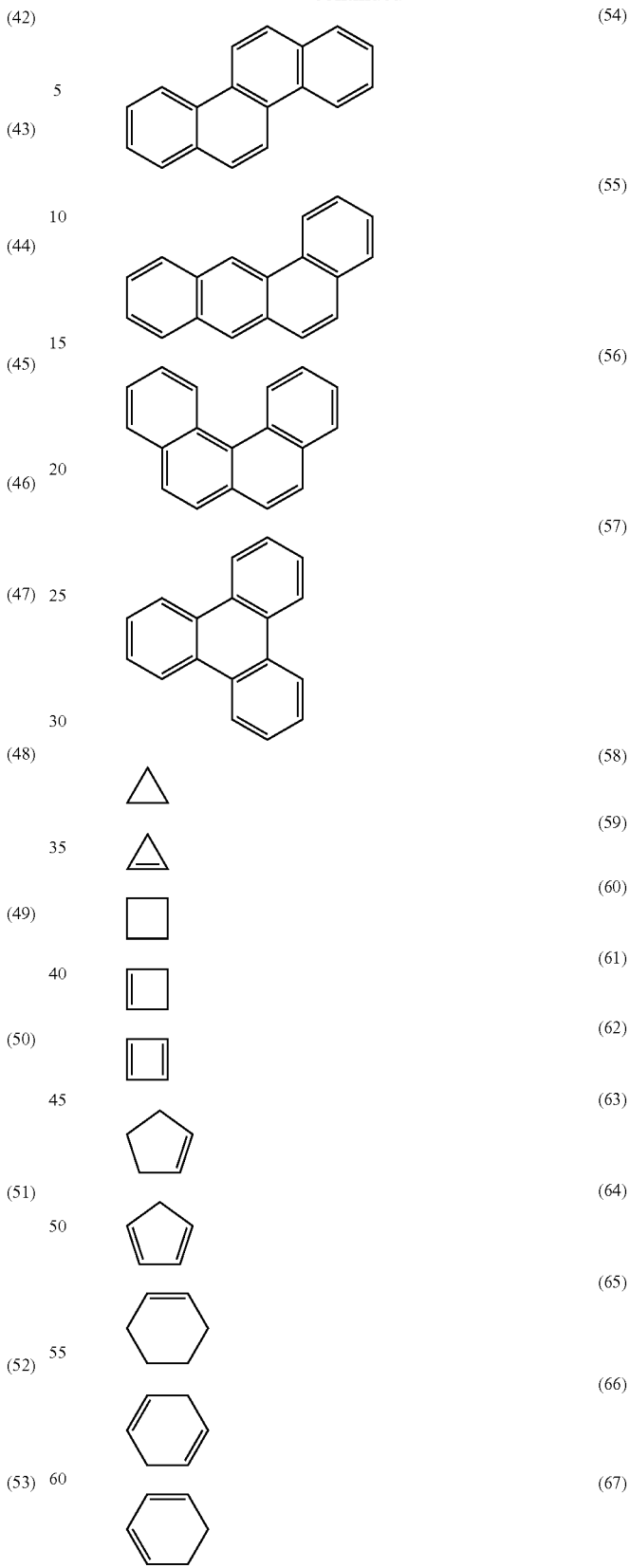
Most preferably, $R^1$-$R^6$ are hydroxyl, C1-6 straight-chain or branched alkyl, C2-6 straight-chain or branched unsaturated hydrocarbon, C1-6 straight-chain or branched alkoxy, C2-6 straight-chain or branched alkanoyloxy, amino, oxyamino, C1-6 straight-chain or branched alkylamino, dialkylamino (where the alkyl group is a C1-6 straight-chain or branched alkyl group), C1-6 straight-chain or branched alkanoylamino, cyano, nitro, sulfo, C1-6 straight-chain or branched alkyl substituted with one or more halogen atoms, C1-6 straight-chain or branched alkoxysulfonyl (where the alkyl group is optionally substituted with one or more halogen atoms), C1-6 straight-chain or branched alkylsulfonyl (where the alkyl group is optionally substituted with one or more halogen atoms), sulfamoyl, C1-6 straight-chain or branched alkylsulfamoyl, carboxyl, carbamoyl, C1-6 straight-chain or branched alkylcarbamoyl, C1-6 straight-chain or branched alkanoyl or C1-6 straight-chain or branched alkoxycarbonyl.

The polymers of the invention must contain a repeating unit represented by general formula (I) or (II), and may optionally contain two or more of the repeating units represented by general formula (I) or (II). They may also contain repeating units represented by general formula (III) or (IV) in addition to the repeating units represented by general formula (I) or (II), and may contain two or more repeating units represented by general formula (III) or (IV). A polymer of the invention preferably contains at least four (more preferably at least six) repeating units represented by general formula (I) or (II).

The polymers of the invention are more preferably polymers containing one or more repeating units represented by general formula (I) or (II), with at least four (more preferably at least six) repeating units represented by any one of formulas (I), (II), (III) and (IV). The polymers of the invention are even more preferably polymers containing two or more repeating units represented by general formula (I) or (II), with at least four (more preferably at least six) repeating units represented by any one of formulas (I), (II), (III) and (IV). A total number of four or more repeating units provides more excellent electron transport properties than with three or fewer, and this is attributed to the fact that a total number of repeating units of four or more results in a polymer with sufficient conjugation length and greater planarity. The upper limit for the total number of repeating units of general formulas (I), (II), (III) and (IV) in the polymer will usually be about 1000.

Figure 9:
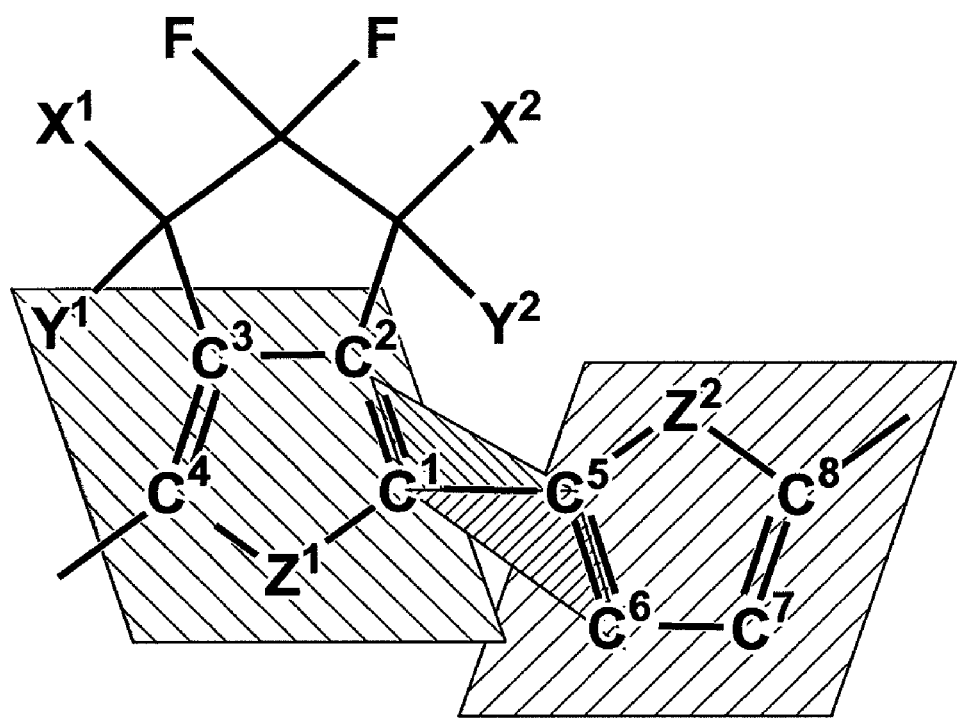
FIG. 9 is a drawing showing the dihedral angle formed between the ring of a repeating unit represented by general formula (II) and the ring of a repeating unit represented by general formula (IV).

When the total number of repeating units represented by general formula (I) or (II) is at least four or the total number of repeating units represented by general formula (I) or (II) and repeating units represented by general formula (III) or (IV) is at least four, the dihedral angles between adjacent aromatic rings or heterocyclic rings are decreased where repeating units represented by general formula (I) or (II) are adjacent to repeating units represented by general formula (III) or (IV), thus improving the intramolecular twist, widening the intramolecular π conjugation and lowering the LUMO level, and enhancing the electron transport property as a result. The dihedral angle is defined as the angle between 0-90 degrees among the angles formed between the plane containing the aromatic ring represented by general formula (I) or (II) and the plane containing its adjacent bonding aromatic ring, and the dihedral angle is usually 0-45 degrees, typically 0-40 degrees and more typically 0-30 degrees. FIG. 9 is a drawing showing the dihedral angle formed between the ring of a repeating unit represented by general formula (II) and the ring of a repeating unit represented by general formula (IV). The dihedral angle is the angle formed between the plane formed by $C^2$—$C^1$—$C^5$ and the plane formed by $C^1$—$C^5$—$C^6$ in FIG. 9. From the standpoint of enhancing the electron transport property, the polymers of the invention are preferably represented by the following formulas (V), (VI), (VII) and (XII).

[Chemical Formula 15]

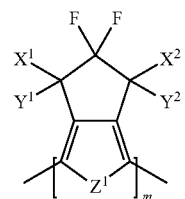

(V)

[Chemical Formula 16]

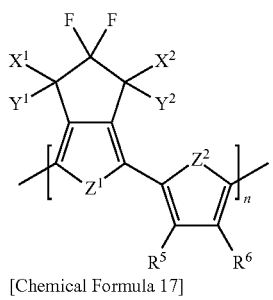

(VI)

[Chemical Formula 17]

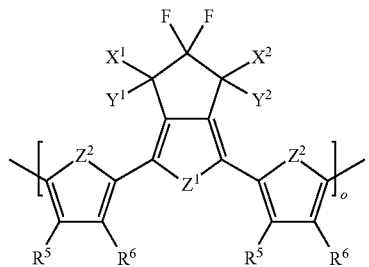

(VII)

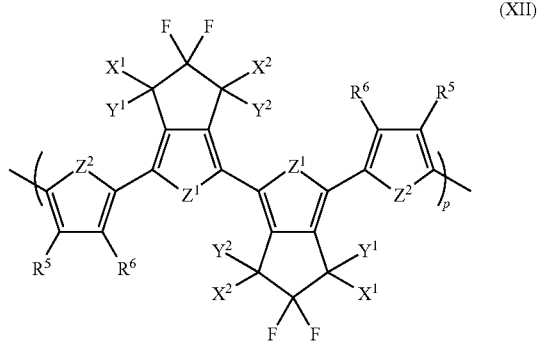

(XII)

$Z^1$, $Z^2$, $X^1$, $Y^1$, $X^2$, $Y^2$, $R^5$ and $R^6$ have the same definitions as above. When a plurality of $Z^1$, $Z^2$, $X^1$, $Y^1$, $X^2$, $Y^2$, $R^5$ and $R^6$ are present, they may be the same or different in each group. The letter m represents an integer of 2-500, preferably 3-20 and even more preferably 4-20. The letter n represents an integer of 1-500 and preferably 2-20. The letter o represents an integer of 1-500 and preferably 1-10. The letter p represents an integer of 1-500, preferably 1-10 and even more preferably 2-10. Most preferred are units where $Z^1$ and $Z^2$ are all sulfur atoms and $X^1$, $Y^1$, $X^2$ and $Y^2$ are all fluorine atoms.

When a polymer of the invention has polymerizing active groups as terminal groups, it may also be used as a polymer precursor. Examples of polymerizing active groups include halogen atoms and alkyl sulfonate, aryl sulfonate, arylalkyl sulfonate, boric acid ester, sulfoniummethyl, phosphoniummethyl, phosphonatemethyl, monohalogenated methyl, boric acid, formyl, trialkyltin and vinyl groups, among which halogen atoms and boric acid ester and trialkyltin groups are preferred.

When a polymer of the invention is to be used as an organic thin-film and polymerizing active groups remain at the ends, they are preferably protected with stable groups to avoid potential reduction in the characteristics and durability of elements formed therefrom.

The terminal groups may be hydrogen, alkyl, alkoxy, fluoroalkyl, fluoroalkoxy, aryl, heterocyclic groups, electron-donating groups or electron-withdrawing groups, among which fluoroalkyl, fluoroalkoxy and electron-withdrawing groups are preferred from the viewpoint of enhancing the electron transport property. They preferably have conjugated bonds that are continuous with the conjugated structure of the main chain, and for example, the structure may comprise bonding with aryl or heterocyclic groups via carbon-carbon bonds.

Most preferred among the polymers of the invention are those represented by the following formulas (68)-(72) and (77)-(90). In general formulas (89) and (90), the repeating units in parentheses may bond randomly to form a random copolymer, alternatingly to form an alternating copolymer, or in a block fashion to form a block copolymer.

[Chemical Formula 18]

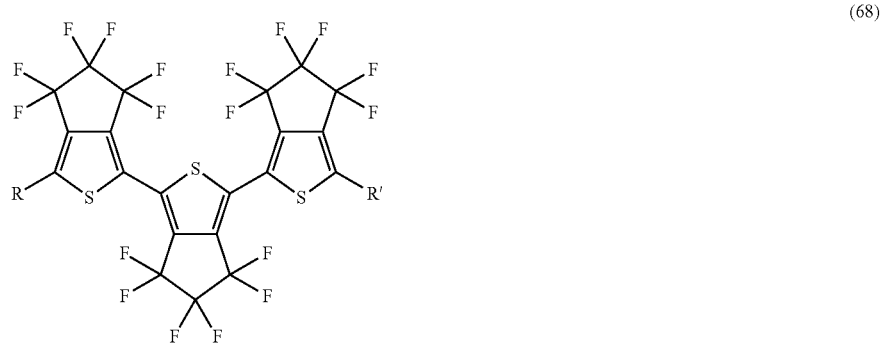

(68)

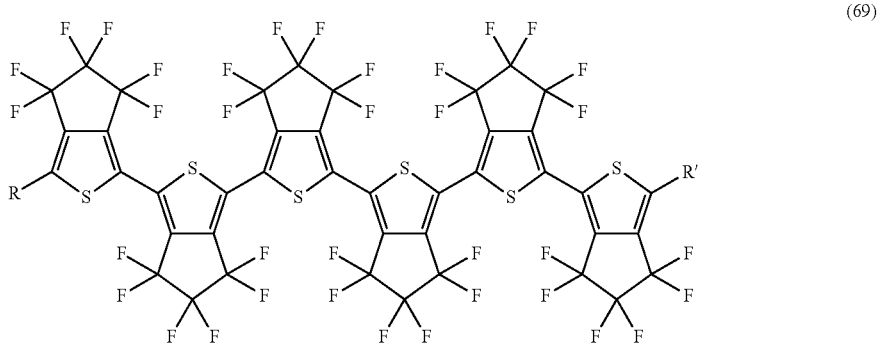

(69)

[Chemical Formula 19]

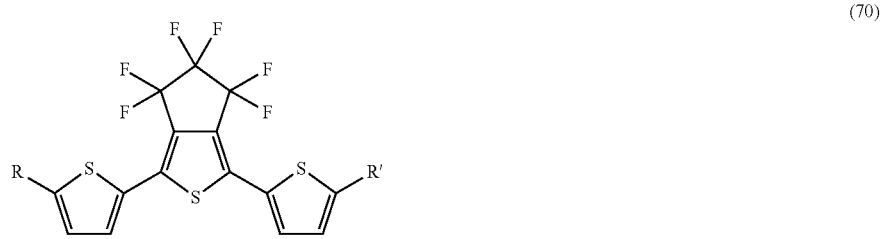

(70)

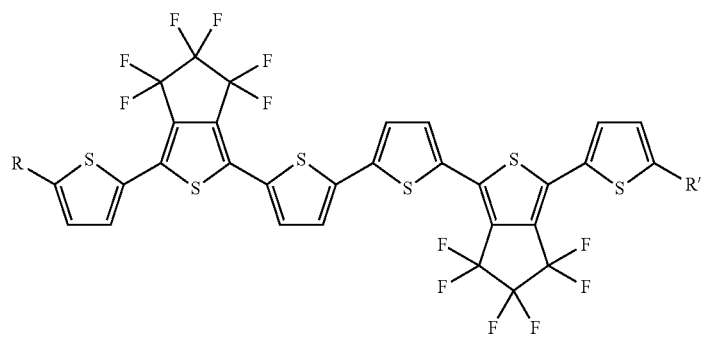

(71)

-continued
[Chemical Formula 20]
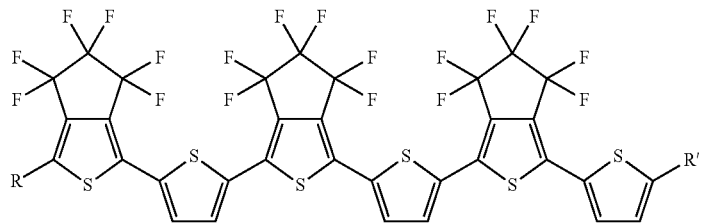
(72)
[Chemical Formula 21]
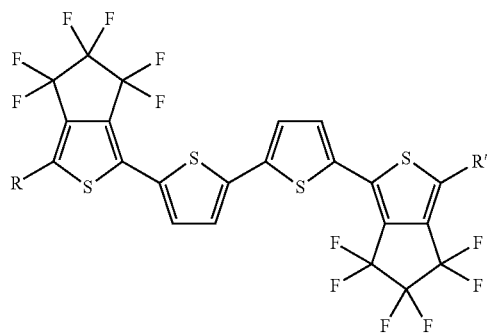
(77)
[Chemical Formula 22]
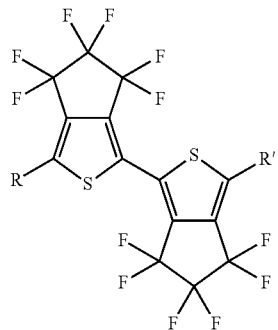
(78)
[Chemical Formula 23]
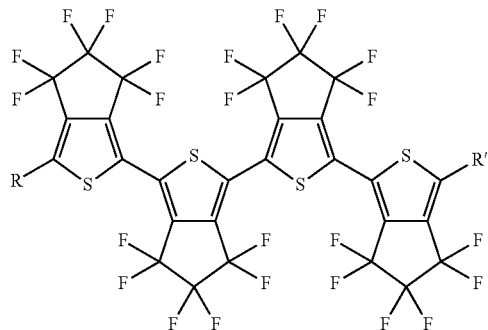
(79)

[Chemical Formula 24]
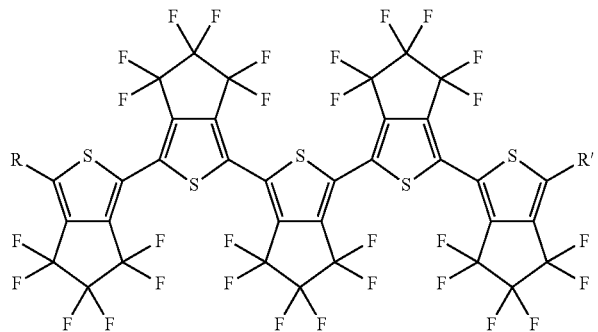
(80)
[Chemical Formula 25]
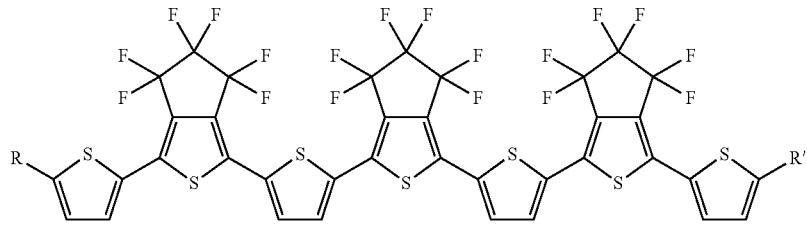
(81)
[Chemical Formula 26]
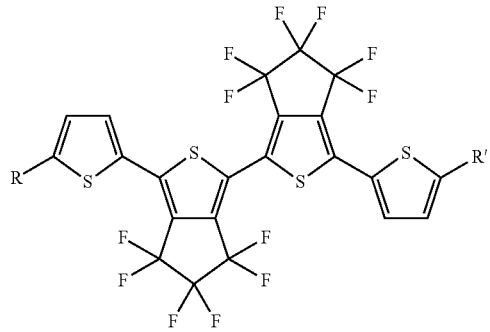
(82)
[Chemical Formula 27]
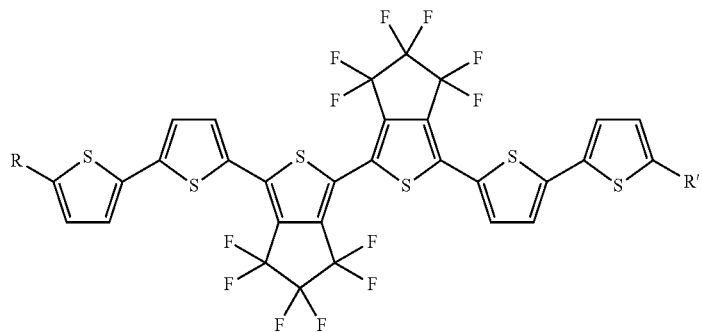
(83)

-continued
[Chemical Formula 28]
(84)
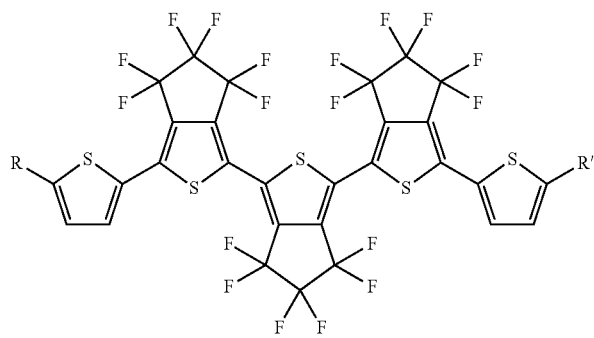
[Chemical Formula 29]
(85)
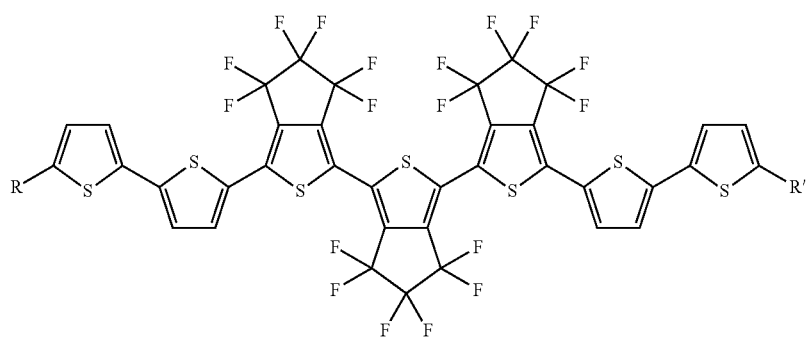
[Chemical Formula 30]
(86)
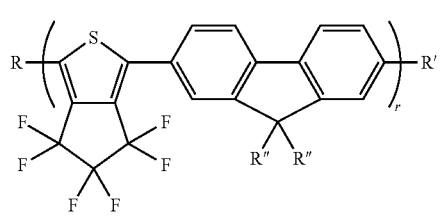
[Chemical Formula 31]
(87)
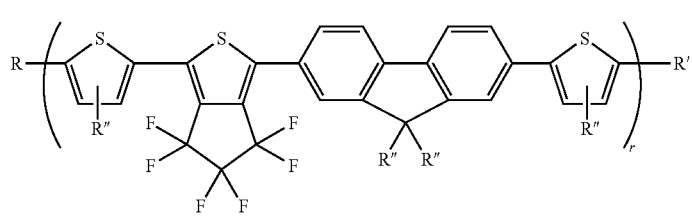
[Chemical Formula 32]
(88)
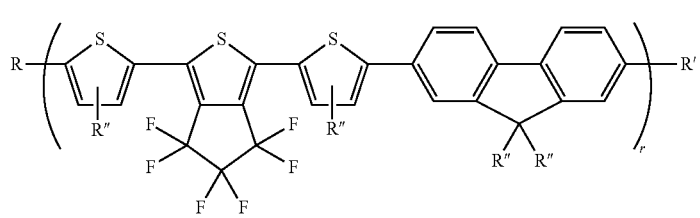

[Chemical Formula 33]

(89)

[Chemical Formula 34]

(90)

R and R' represent terminal groups, which may be the same or different and have as examples the groups mentioned above, with fluoroalkyl groups being preferred. The R″ groups each independently represent hydrogen or an optional substituent, among which alkyl, alkoxy, aryl and arylalkyl groups are preferred and alkyl and aryl groups are more preferred. The letters r and t each represent an integer of 1-500 and preferably 1-200, and they are preferably integers of 1-10 when the polymer is an oligomer or integers of 20-200 when the polymer is a long polymer.

When the polymer of the invention is an oligomer, it preferably has 2-10 and more preferably 4-10 repeating units represented by general formula (I)-(IV). When the polymer of the invention is a polymer with a larger molecular weight than an oligomer, the polystyrene-based number-average molecular weight is preferably $10^3$-$10^8$ and more preferably $10^3$-$10^6$.

A process for production of polymers according to the invention will now be explained. The polymers of the invention may be produced, for example, by a reaction wherein the starting materials are compounds represented by the following general formulas (VIIIa)-(XIa) and (VIIIb)-(XIb).

[Chemical Formula 35]

(VIII a)

(VIII b)

[Chemical Formula 36]

(IX a)

(IX b)

[Chemical Formula 37]

$W^1$—$Ar^2$  (X a)

$W^1$—$Ar^2$—$W^2$  (X b)

[Chemical Formula 38]

(XI a)

(XI b)

In general formulas (VIIIa)-(XIa) and (VIIIb)-(XIb) above, $Ar^1, Ar^2, X^1, Y^1, X^2, Y^2, Z^1, Z^2, R^5$ and $R^6$ are the same groups as previously defined. $W^1$ and $W^2$ each independently represent a halogen atom or an alkyl sulfonate, aryl sulfonate, arylalkyl sulfonate, boric acid ester, sulfoniummethyl, phosphoniummethyl, phosphonatemethyl, monohalogenated methyl, boric acid, formyl, trialkyltin or vinyl group.

From the viewpoint of facilitating synthesis and reaction of the compounds represented by general formulas (VIIIa)-(XIa) and (VIIIb)-(XIb), preferably $W^1$ and $W^2$ each independently represent a halogen atom or an alkyl sulfonate, aryl sulfonate, arylalkyl sulfonate, boric acid ester, boric acid or trialkyltin group.

Examples of reaction processes that may be used for production of polymers of the invention include processes employing Suzuki coupling reaction, processes employing Grignard reaction, processes employing Stille reaction, processes employing Ni(0) catalysts, processes employing oxidizing agents such as $FeCl_3$, processes employing anionic oxidation, processes employing palladium acetate and an organic base, processes involving preparation of a lithiated derivative from an α-unsubstituted or halogenated compound, and oxidative coupling, processes employing electrochemical oxidation and processes involving decomposition of an intermediate compound with an appropriate leaving group.

Of these, processes employing Suzuki coupling reaction, processes employing Grignard reaction, processes employing Stille reaction, processes employing Ni(0) catalysts, processes employing anionic oxidation and processes employing palladium acetate and an organic base are preferred for easier structural control, ready availability and simplification of the reaction procedure.

The catalyst used for Suzuki coupling reaction may be palladium[tetrakis(triphenylphosphine)] or palladium acetate, for example, with addition of at least one equivalent and preferably 1-10 equivalents of an inorganic base such as potassium carbonate, sodium carbonate or barium hydroxide, an organic base such as triethylamine or an inorganic salt such as cesium fluoride, with respect to the monomer. The reaction may be carried out in a two-phase system, with the inorganic salt in aqueous solution. As examples of solvents there may be mentioned N,N-dimethylformamide, toluene, dimethoxyethane and tetrahydrofuran. The reaction temperature will depend on the solvent used but is preferably about 50-160° C. The temperature may be increased to near the boiling point of the solvent for reflux, and the reaction time will generally be between 1 hour and 200 hours. The Suzuki coupling reaction is described in, for example, Chem. Rev. Vol. 95, p. 2457 (1995).

A reaction employing a Ni(0) catalyst will now be explained. The process may employ a zerovalent nickel complex as the Ni(0) catalyst, or it may include reacting a nickel salt in the presence of a reducing agent to produce zerovalent nickel in the system. Examples of zerovalent nickel complexes include bis(1,5-cyclooctadiene)nickel(0), (ethylene)bis(triphenylphosphine)nickel(0) and tetrakis(triphenylphosphine)nickel, among which bis(1,5-cyclooctadiene)nickel(0) is preferred from the viewpoint of greater flexibility of use and lower cost.

Addition of a neutral ligand during the reaction is also preferred from the viewpoint of increasing the yield. A "neutral ligand" is a ligand containing no anions or cations, and examples thereof include nitrogen-containing ligands such as 2,2'-bipyridyl, 1,10-phenanthroline, methylenebisoxazoline and N,N'-tetramethylethylenediamine, and tertiary phosphine ligands such as triphenylphosphine, tritolylphosphine, tributylphosphine and triphenoxyphosphine. Nitrogen-containing ligands are preferred from the viewpoint of greater flexibility and lower cost, while 2,2'-bipyridyl is especially preferred from the viewpoint of higher reactivity and yield. For increased polymer yield, a system containing 2,2'-bipyridyl added as a neutral ligand to a system containing bis(1,5-cyclooctadiene)nickel(0) is especially preferred. As nickel salts to be used in the process for producing zerovalent nickel in the system there may be mentioned nickel chloride and nickel acetate. As reducing agents there may be mentioned zinc, sodium hydride, hydrazine and their derivatives, and also lithium aluminum hydride. Ammonium iodide, lithium iodide, potassium iodide and the like may also be used as additives when necessary.

For Stille reaction, a catalyst such as palladium [tetrakis(triphenylphosphine)] or palladium acetate may be used, and the reaction may be conducted using an organic tin compound as monomer. As examples of solvents there may be mentioned N,N-dimethylformamide, toluene, dimethoxyethane and tetrahydrofuran. The reaction temperature will depend on the solvent used but is preferably about 50-160° C. The temperature may be increased to near the boiling point of the solvent for reflux. The reaction time will be between 1 hour and 200 hours.

For a process employing anionic oxidation reaction, a halogen- or hydrogen-substituted compound may be used as the monomer for reaction with n-butyllithium to prepare a lithiated derivative, which is then treated with an oxidizing agent such as copper(II) bromide, copper(II) chloride, iron(III) acetylacetonate or the like. Examples of solvents include toluene, dimethoxyethane, tetrahydrofuran, hexane, heptane and octane. The reaction temperature will depend on the solvent used but is preferably about 50-160° C. The temperature may be increased to near the boiling point of the solvent for reflux. The reaction time will generally be between 5 minutes and 200 hours.

For a process employing palladium acetate and an organic base, a halogen-substituted compound may be used as the monomer and palladium(II) acetate and an organic base such as diisopropylamine or triethylamine added for reaction. As examples of solvents there may be mentioned N,N-dimethylformamide, toluene, dimethoxyethane and tetrahydrofuran. The reaction temperature will depend on the solvent used but is preferably about 50-160° C. The temperature may be increased to near the boiling point of the solvent for reflux. The reaction time will generally be between 5 minutes and 200 hours.

For production of an oligomer having four or more repeating units as a polymer according to the invention, the reaction may be carried out with selection of a combination of substituents that contribute to condensation polymerization of the monomers, and selection of the type of polymerization reaction employed. For example, after synthesizing an oligomer having two or more repeating units, polymerizing active groups may be introduced into the oligomer to create a monomer, and this monomer may be polymerized either with itself or with another monomer.

When a high-molecular-weight polymer is synthesized as a polymer of the invention, a monomer having at least two polymerizing active groups may be used and the reaction may be carried out with selection of a combination of substituents that contribute to condensation polymerization of the monomer, and selection of the type of polymerization reaction employed. From the viewpoint of avoiding reduction in solubility in organic solvents and increasing the polymerization degree, it is preferred to use a monomer having two polymerizing active groups, examples of which include monomers of general formulas (VIIIb)-(XIb) above. It is also preferred to use a monomer comprising the structure of general formula (Xb) or (XIb) in addition to a monomer comprising the structure of general formula (VIIIb) or (IXb). A monomer comprising the structure of general formula (Xb) or (XIb) most preferably has substituents.

When a polymer according to the invention has an asymmetrical backbone in the repeating unit, the repeating units of the polymer will have directionality. The directionality of the repeating units can be controlled in the polymerization by selecting the combination of substituents that contribute to condensation polymerization of the monomer, and selecting the type of polymerization reaction employed.

In order to control the sequence of two or more repeating units in a polymer of the invention, polymerization may be conducted after synthesizing an oligomer having all or a portion of the repeating units in the desired sequence, or the sequence of repeating units may be controlled for polymerization by selecting the substituents that contribute to condensation polymerization of each of the monomers, and selecting the type of polymerization reaction employed.

When $Z^1$ and $Z^2$ in general formula (I) or (IV) for a polymer of the invention are represented by formulas (i), (vi) or (vii), polymerization is preferably carried out by Stille reaction.

For synthesis of a random copolymer as a polymer of the invention, polymerization may be conducted selecting the same polymerizing active groups as substituents that contribute to condensation polymerization of each of the monomers used, and selecting the polymerization reaction employed. For example, there may be mentioned a process wherein bromine is selected as the polymerizing active group and Ni(0) is used as the catalyst.

For synthesis of an alternating copolymer represented by any of general formulas (86)-(88) as a polymer of the invention, at least two different monomers may be used, and the sequence of repeating units may be controlled in the polymerization by selecting polymerizing active groups with different substituents that contribute to condensation polymerization of each of the monomers used, and selecting the type of polymerization reaction employed. For example, bromine may be selected as one of the polymerizing active groups while a boric acid ester is selected as another polymerizing active group for Suzuki coupling reaction, or bromine may be selected as one of the polymerizing active groups while trialkyltin is selected as another polymerizing active group for Stille reaction.

For synthesis of a block copolymer represented by general formula (89) or (90) as a polymer of the invention, reaction of a random copolymer or alternating copolymer may be followed by addition of another new monomer and further polymerization without inactivating the terminal polymerizing active groups.

When a compound represented by any of general formulas (VIIIa)-(XIa) or (VIIIb)-(XIb) is used as monomer, it may be dissolved in an organic solvent if necessary and reacted between the melting point and boiling point of the organic solvent using an alkali or appropriate catalyst, for example.

The organic solvent used will differ depending on the compounds and reaction employed, but in order to limit secondary reactions it is generally preferred to be one that accomplishes sufficient deoxygenation treatment and promotes the reaction in an inert atmosphere. It is also preferably one that accomplishes dehydration treatment. (This does not apply, however, for reactions conducted in a two-phase system with water, such as Suzuki coupling.)

A suitable alkali or catalyst is added for the reaction, and these may be selected as appropriate for the reaction employed. The alkali or catalyst is preferably one that thoroughly dissolves in the solvent used for the reaction.

When a polymer of the invention is to be used as a material for an organic thin-film element, the monomer is preferably polymerized after purification by a method such as distillation, sublimation purification or recrystallization since the purity will affect the element characteristics. After synthesis of the polymer, it is preferably subjected to purifying treatment such as separation by reprecipitation or chromatography.

As examples of solvents to be used for the reaction there may be mentioned saturated hydrocarbons such as pentane, hexane, heptane, octane and cyclohexane, unsaturated hydrocarbons such as benzene, toluene, ethylbenzene and xylene, halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane, halogenated unsaturated hydrocarbons such as chlorobenzene, dichlorobenzene and trichlorobenzene, alcohols such as methanol, ethanol, propanol, isopropanol, butanol and t-butyl alcohol, carboxylic acids such as formic acid, acetic acid and propionic acid, ethers such as dimethyl ether, diethyl ether, methyl-t-butyl ether, tetrahydrofuran, tetrahydropyran, dioxane, and inorganic acids such as hydrochloric acid, hydrobromic acid, hydrofluoric acid, sulfuric acid and nitric acid. A single solvent or a mixture of these solvents may be used.

The reaction may be followed by ordinary post-treatment such as, for example, quenching with water, subsequent extraction with an organic solvent and distillation of the solvent. Isolation and purification of the product can be carried out by chromatographic fractionation or recrystallization.

An organic thin-film according to the invention will now be explained. An organic thin-film of the invention is characterized by comprising a polymer of the invention.

The film thickness of the organic thin-film will usually be about 1 nm-100 μm, preferably 2 nm-1000 nm, even more preferably 5 nm-500 nm and most preferably 20 nm-200 nm.

The organic thin-film may contain only one of the aforementioned polymers, or it may include two or more of such polymers. In order to enhance the electron transport and hole transport properties of the organic thin-film, a low molecular compound or high molecular compound having an electron transport or hole transport property may also be combined with the polymer.

Any publicly known hole transporting material may be used, and examples include pyrazoline derivatives, arylamine derivatives, stilbene derivatives, triaryldiamine derivatives, oligothiophenes and their derivatives, polyvinylcarbazole and its derivatives, polysilane and its derivatives, polysiloxane derivatives with aromatic amines on side chains or the main chain, polyaniline and its derivatives, polythiophene and its derivatives, polypyrrole and its derivatives, polyarylenevinylenes and its derivatives and polythienylenevinylene and its derivatives. Any publicly known electron transporting materials may also be used, and examples include oxadiazole derivatives, anthraquinodimethane and its derivatives, benzoquinone and its derivatives, naphthoquinone and its derivatives, anthraquinone and its derivatives, tetracyanoanthraquinodimethane and its derivatives, fluorenone derivatives, diphenyldicyanoethylene and its derivatives, diphenoquinone derivatives or 8-hydroxyquinoline and metal complexes of its derivatives, or polyquinoline and its derivatives, polyquinoxaline and its derivatives, polyfluorene and its derivatives, $C_{60}$ and other fullerenes, and derivatives thereof.

An organic thin-film of the invention may also contain a charge generation material for generation of a charge upon absorption of light in the organic thin-film. Any publicly known charge generation material may be used, including azo compounds and their derivatives, diazo compounds and their derivatives, ametallic phthalocyanine compounds and their derivatives, metallic phthalocyanine compounds and their derivatives, perylene compounds and their derivatives, polycyclic quinone-based compounds and their derivatives, squarylium compounds and their derivatives, azulenium compounds and their derivatives, thiapyrylium compounds and their derivatives, and $C_{60}$ or other fullerenes and their derivatives.

The organic thin-film of the invention may also contain materials necessary for exhibiting various functions. As examples there may be mentioned sensitizing agents to enhance the function of generating charge by light absorption, stabilizers to increase stability, and UV absorbers for absorption of UV light.

The organic thin-film of the invention may also contain high molecular compound materials as macromolecular binders in addition to the polymer mentioned above, in order to improve the mechanical properties. As high molecular binders there are preferably used ones that produce minimal interference with the electron transport or hole transport property, and ones with weak absorption for visible light.

Examples of such high molecular binders include poly(N-vinylcarbazole), polyaniline and its derivatives, polythiophene and its derivatives, poly(p-phenylenevinylene) and its derivatives, poly(2,5-thienylenevinylene) and its derivatives, polycarbonates, polyacrylates, polymethyl acrylate, polymethyl methacrylate, polystyrene, polyvinyl chloride, polysiloxane and the like.

There are no particular restrictions on the process for production of a organic thin-film of the invention, and for example, there may be employed a process of film formation from a solution comprising the polymer and, as necessary, an electron transport or hole transporting material and a high molecular binder in admixture therewith. A thin-film can be formed by vacuum vapor deposition when using an oligomer according to the invention.

The solvent used for film formation from a solution is not particularly restricted so long as it dissolves the polymer and the electron transporting or hole transporting materials and high molecular binders combined therewith.

Examples of solvents to be used for film formation of an organic thin-film of the invention from a solution include unsaturated hydrocarbon-based solvents such as toluene, xylene, mesitylene, tetralin, decalin, bicyclohexyl, n-butylbenzene, sec-butylbenzene and tert-butylbenzene, halogenated saturated hydrocarbon-based solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane, halogenated unsaturated hydrocarbon-based solvents such as chlorobenzene, dichlorobenzene and trichlorobenzene, and ether-based solvents such as tetrahydrofuran and tetrahydropyran. Dissolution in such solvents will normally be to at least 0.1 wt %, although this will differ depending on the structure and molecular weight of the polymer.

The method of forming the film from the solution may be a coating method such as spin coating, casting, microgravure coating, gravure coating, bar coating, roll coating, wire bar coating, dip coating, spray coating, screen printing, flexographic printing, offset printing, ink jet printing, dispenser printing or the like, among which spin coating, flexographic printing, ink jet printing and dispenser printing method are preferred.

The steps for production of an organic thin-film of the invention may include a step of orienting the oligomer or polymer. An organic thin-film with high molecular compound orientation in such a step will have the main chain molecules or side chain molecules aligned in a single direction, thus improving the electron mobility or hole mobility.

The method of orienting the high molecular compound may be a known method for orienting liquid crystals. Rubbing, photoorientation, shearing (shear stress application) and pull-up coating methods are convenient, useful and easy orienting methods, with rubbing and shearing being preferred.

Since the organic thin-film of the invention has an electron transport or hole transport property, the transport of electrons or holes introduced from the electrode or charge generated by photoabsorption can be controlled for use in various organic thin-film elements such as organic thin-film transistors, organic solar cells, optical sensors and the like. When the organic thin-film is used in such organic thin-film elements, it is preferably used after orientation by orienting treatment for enhanced electron transport or hole transport properties.

Also, since the organic thin-film of the invention has an electron transport property, the transport of electrons introduced from the electrode or charge generated by photoabsorption can be controlled for use in various organic thin-film elements such as organic electroluminescent elements, organic transistors, organic solar cells, optical sensors and the like.

Application of an organic thin-film of the invention to an organic thin-film transistor will now be explained. The organic thin-film transistor may have a structure comprising a source electrode and drain electrode, an organic thin-film layer (active layer) containing a polymer according to the invention which acts as a current channel between them, and a gate electrode that controls the level of current flowing through the current channel; the transistor may be a field-effect type or static induction type, for example.

A field-effect organic thin-film transistor preferably has a structure comprising a source electrode and drain electrode, an organic thin-film layer (active layer) containing a polymer according to the invention which acts as a current channel between them, a gate electrode that controls the level of current flowing through the current channel, and an insulating layer situated between the active layer and the gate electrode. Most preferably, the source electrode and drain electrode are provided in contact with the organic thin-film layer (active layer) containing the polymer of the invention, and the gate electrode is provided sandwiching the insulating layer which is also in contact with the organic thin-film layer.

A static induction organic thin-film transistor has a structure comprising a source electrode and drain electrode, an organic thin-film layer containing a high molecular compound according to the invention which acts as a current channel between them and a gate electrode that controls the level of current flowing through the current channel, preferably with the gate electrode in the organic thin-film layer. Most preferably, the source electrode, the drain electrode and the gate electrode formed in the organic thin-film layer are provided in contact with the organic thin-film layer containing the polymer of the invention. The structure of the gate electrode may be any one that forms a current channel for flow from the source electrode to the drain electrode, and that allows the level of current flowing through the current channel to be controlled by the voltage applied to the gate electrode; an example of such a structure is a combshaped electrode.

FIG. 1 is a schematic cross-sectional view of an organic thin-film transistor (field-effect organic thin-film transistor) according to a first embodiment. The organic thin-film transistor 100 shown in FIG. 1 comprises a substrate 1, a source electrode 5 and drain electrode 6 formed at a prescribed spacing on the substrate 1, an active layer 2 formed on the substrate 1 covering the source electrode 5 and drain electrode 6, an insulating layer 3 formed on the active layer 2, and a gate electrode 4 formed on the insulating layer 3 covering the region of the insulating layer 3 between the source electrode 5 and drain electrode 6.

Figure 2:
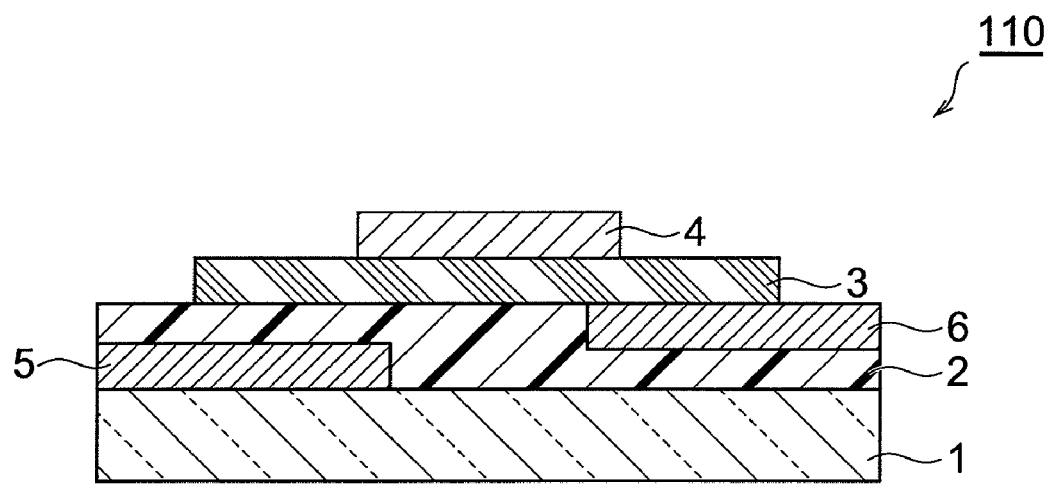
FIG. 2 is a schematic cross-sectional view of an organic thin-film transistor according to a second embodiment.

FIG. 2 is a schematic cross-sectional view of an organic thin-film transistor (field-effect organic thin-film transistor) according to a second embodiment. The organic thin-film transistor 110 shown in FIG. 2 comprises a substrate 1, a source electrode 5 formed on the substrate 1, an active layer 2 formed on the substrate 1 covering the source electrode 5, a drain electrode 6 formed on the active layer 2 at a prescribed spacing from the source electrode 5, an insulating layer 3 formed on the active layer 2 and drain electrode 6, and a gate electrode 4 formed on the insulating layer 3 covering the region of the insulating layer 3 between the source electrode 5 and drain electrode 6.

Figure 3:
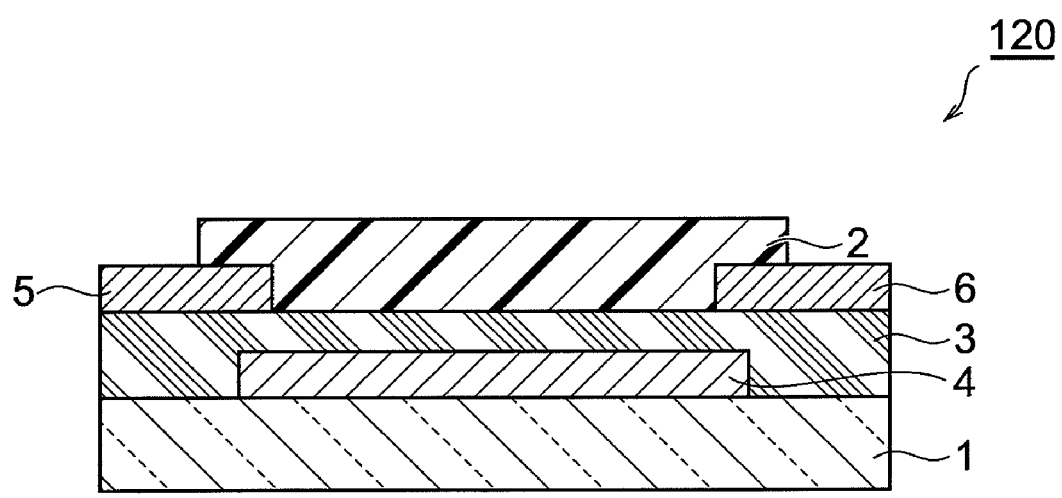
FIG. 3 is a schematic cross-sectional view of an organic thin-film transistor according to a third embodiment.

FIG. 3 is a schematic cross-sectional view of an organic thin-film transistor (field-effect organic thin-film transistor) according to a third embodiment. The organic thin-film transistor 120 shown in FIG. 3 comprises a substrate 1, a gate electrode 4 formed on the substrate 1, an insulating layer 3 formed on the substrate 1 covering the gate electrode 4, a source electrode 5 and drain electrode 6 formed at a prescribed spacing on the insulating layer 3 covering portions of the region of the insulating layer 3 under which the gate electrode 4 is formed, and an active layer 2 formed on the insulating layer 3 covering the source electrode 5 and drain electrode 6.

Figure 4:
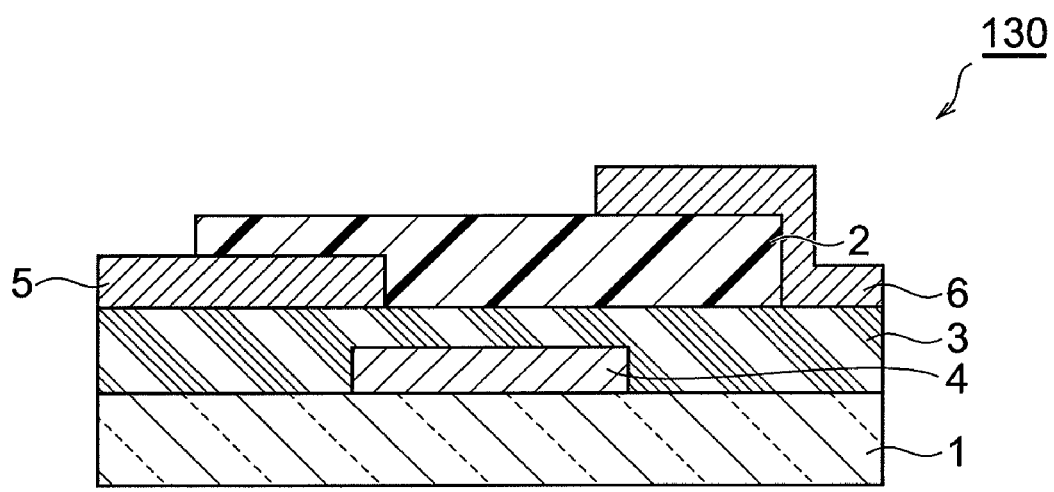
FIG. 4 is a schematic cross-sectional view of an organic thin-film transistor according to a fourth embodiment.

FIG. 4 is a schematic cross-sectional view of an organic thin-film transistor (field-effect organic thin-film transistor) according to a fourth embodiment. The organic thin-film transistor 130 shown in FIG. 4 comprises a substrate 1, a gate electrode 4 formed on the substrate 1, an insulating layer 3 formed on the substrate 1 covering the gate electrode 4, a source electrode 5 formed on the insulating layer 3 covering a portion of the region of the insulating layer 3 under which the gate electrode 4 is formed, an active layer 2 formed on the insulating layer 3 covering the source electrode 5, and a drain electrode 6 formed on the insulating layer 3 at a prescribed spacing from the source electrode 5 and covering a portion of the region of the active layer 2 under which the gate electrode 4 is formed.

Figure 10:
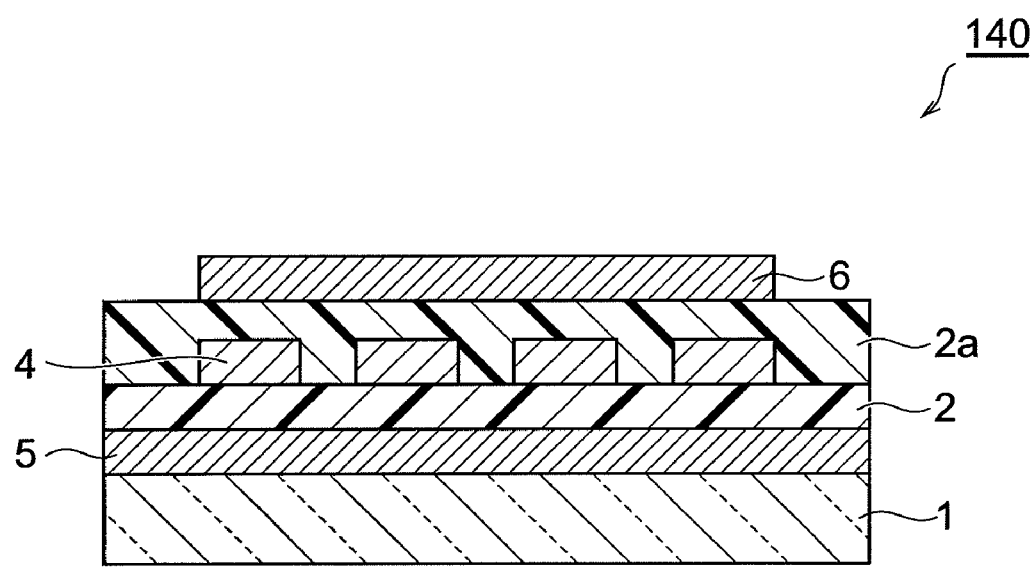
FIG. 10 is a schematic cross-sectional view of an organic thin-film transistor according to a fifth embodiment.

FIG. 10 is a schematic cross-sectional view of an organic thin-film transistor (static induction organic thin-film transistor) according to a fifth embodiment. The organic thin-film transistor 140 shown in FIG. 10 comprises a substrate 1, a source electrode 5 formed on the substrate 1, an active layer 2 formed on the source electrode 5, a plurality of gate electrodes 4 formed at prescribed spacings on the active layer 2, an active layer 2a formed on the active layer 2 covering all of the gate electrodes 4, (the material composing the active layer 2a may be the same as or different from that of the active layer 2) and a drain electrode 6 formed on the active layer 2a.

Figure 11:
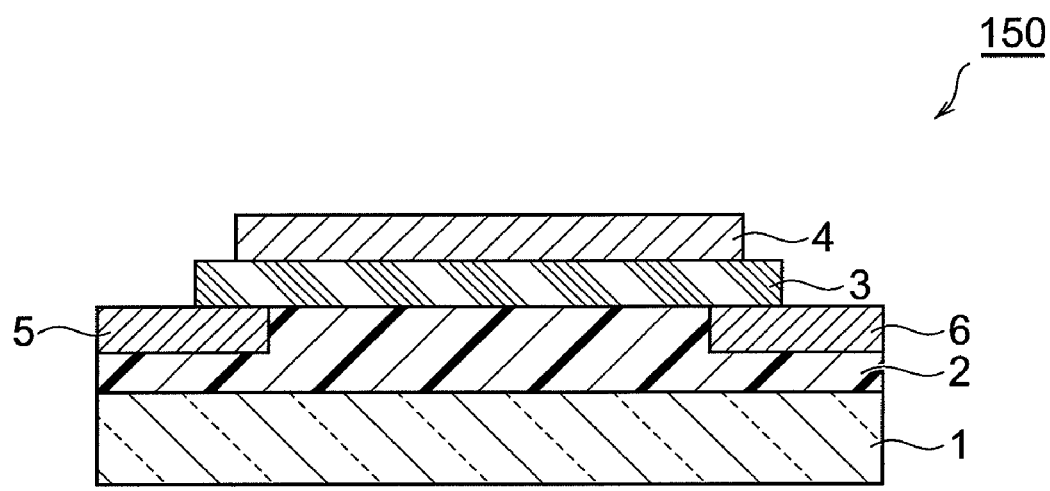
FIG. 11 is a schematic cross-sectional view of an organic thin-film transistor according to a sixth embodiment.

FIG. 11 is a schematic cross-sectional view of an organic thin-film transistor (field-effect organic thin-film transistor) according to a sixth embodiment. The organic thin-film transistor 150 shown in FIG. 11 comprises a substrate 1, an active layer 2 formed on the substrate 1, a source electrode 5 and drain electrode 6 formed at a prescribed spacing on the active layer 2, an insulating layer 3 formed on the active layer 2 covering the source electrode 5 and drain electrode 6, and a gate electrode 4 formed on the insulating layer 3, covering a portion of the region of the insulating layer 3 under which the source electrode 5 is formed and a portion of the region of the insulating layer 3 under which the drain electrode 6 is formed.

Figure 12:
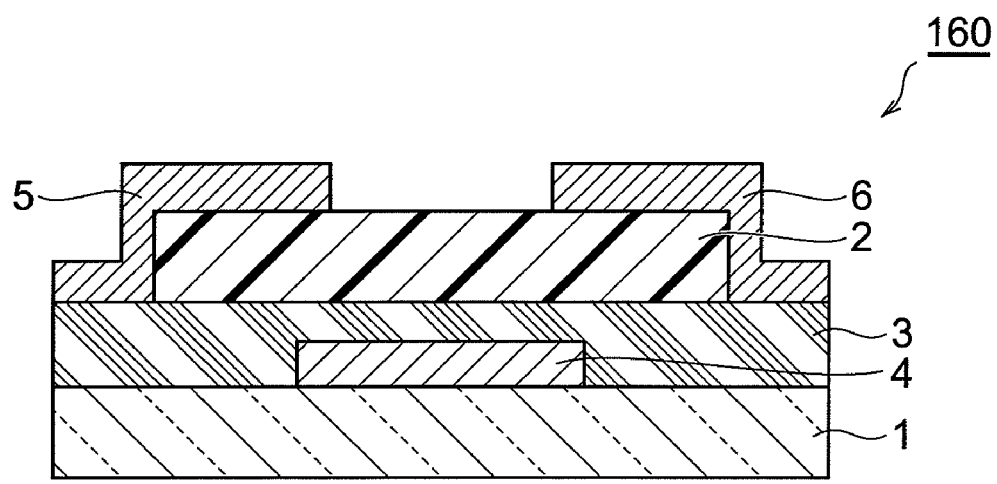
FIG. 12 is a schematic cross-sectional view of an organic thin-film transistor according to a seventh embodiment.

FIG. 12 is a schematic cross-sectional view of an organic thin-film transistor (field-effect organic thin-film transistor) according to a seventh embodiment. The organic thin-film transistor 160 shown in FIG. 12 comprises a substrate 1, a gate electrode 4 formed on the substrate 1, an insulating layer 3 formed on the substrate 1 covering the gate electrode 4, an active layer 2 formed covering the region of the insulating layer 3 under which the gate electrode 4 is formed, a source electrode 5 formed on the insulating layer 3 covering a portion of the region of the active layer 2 under which the gate electrode 4 is formed, and a drain electrode 6 formed on the insulating layer 3 at a prescribed spacing from the source electrode 5 and covering a portion of the region of the active layer 2 under which the gate electrode 4 is formed.

In the organic thin-film transistors of the first to seventh embodiments described above, the active layer 2 and/or the active layer 2a contains a polymer according to the invention and forms a current channel between the source electrode 5 and drain electrode 6. The gate electrode 4 controls the level of current flowing through the current channel of the active layer 2 and/or active layer 2a by application of voltage.

This type of field-effect organic thin-film transistor can be manufactured by a publicly known process, such as the process described in Japanese Unexamined Patent Publication HEI No. 5-110069, for example. The static induction organic thin-film transistor can also be manufactured by a publicly known process such as the process described in Japanese Unexamined Patent Publication No. 2004-006476, for example.

The material of the substrate 1 is not particularly restricted so long as it does not impair the characteristics of the organic thin-film transistor, and a glass substrate, flexible film substrate or plastic substrate may be used.

Since organic solvent-soluble compounds are highly advantageous and preferred in forming the active layer 2, the organic thin-film production process of the invention described above may be used to form organic thin-films composed of the active layer 2.

The insulating layer 3 in contact with the active layer 2 is not particularly restricted so long as it is a material with high electrical insulating properties, and any publicly known one may be used. As examples there may be mentioned SiOx, SiNx, $Ta_2O_5$, polyimide, polyvinyl alcohol, polyvinylphenol and organic glass. From the viewpoint of achieving low voltage, a material with high permittivity is preferred.

When the active layer 2 is formed on the insulating layer 3, it may be formed after surface modification by treatment of the surface of the insulating layer 3 with a surface treatment agent such as a silane coupling agent in order to improve the interfacial properties between the insulating layer 3 and active layer 2. As surface treatment agents there may be mentioned long-chain alkylchlorosilanes, long-chain alkylalkoxysilanes, fluorinated alkylchlorosilanes, fluorinated alkylalkoxysilanes and silylamine compounds such as hexamethyldisilazane. Before treatment with the surface treatment agent, the insulating layer surface may be pre-treated by ozone UV or $O_2$ plasma.

After the organic thin-film transistor has been fabricated, a protecting film is preferably formed on the organic thin-film transistor to protect the element. This will help prevent reduction in the characteristics of the organic thin-film transistor when it is exposed to air. A protecting film can also minimize adverse effects when an operating display device is formed on the organic thin-film transistor.

The method of forming the protecting film may involve covering with a UV cured resin, thermosetting resin, inorganic SiONx film or the like. For effective shielding from air, the steps after fabrication of the organic thin-film transistor and before formation of the protecting film are preferably carried out without exposure to air (for example, in a dry nitrogen atmosphere or in a vacuum).

Application of an organic thin-film of the invention in a solar cell will now be explained.

Figure 5:
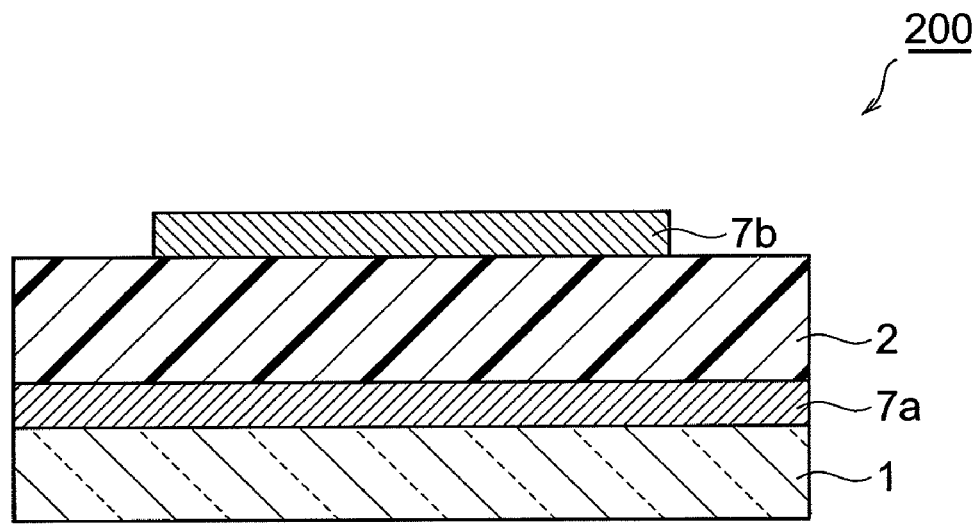
FIG. 5 is a schematic cross-sectional view of a solar cell according to an embodiment of the invention.

FIG. 5 is a schematic cross-sectional view of a solar cell according to an embodiment of the invention. The solar cell 200 shown in FIG. 5 comprises a substrate 1, a first electrode 7a formed on the substrate 1, an active layer 2 comprising an organic thin-film that contains a polymer of the invention formed on the first electrode 7a, and a second electrode 7b formed on the active layer 2.

In the solar cell of this embodiment, a transparent or semi-transparent electrode is used for either or both the first electrode 7a and second electrode 7b. As electrode materials there may be used metals such as aluminum, gold, silver, copper, alkali metal and alkaline earth metals or their semi-transparent films, or transparent conductive films. In order to obtain high open voltage, it is preferred to select the electrodes so as to produce a large work function difference. Carrier generators, sensitizing agents and the like may also be added in order to increase photosensitivity in the active layer 2 (organic thin-film). The substrate 1 may be a silicon substrate, glass substrate, plastic substrate or the like.

Application of an organic thin-film of the invention in an optical sensor will now be explained.

Figure 6:
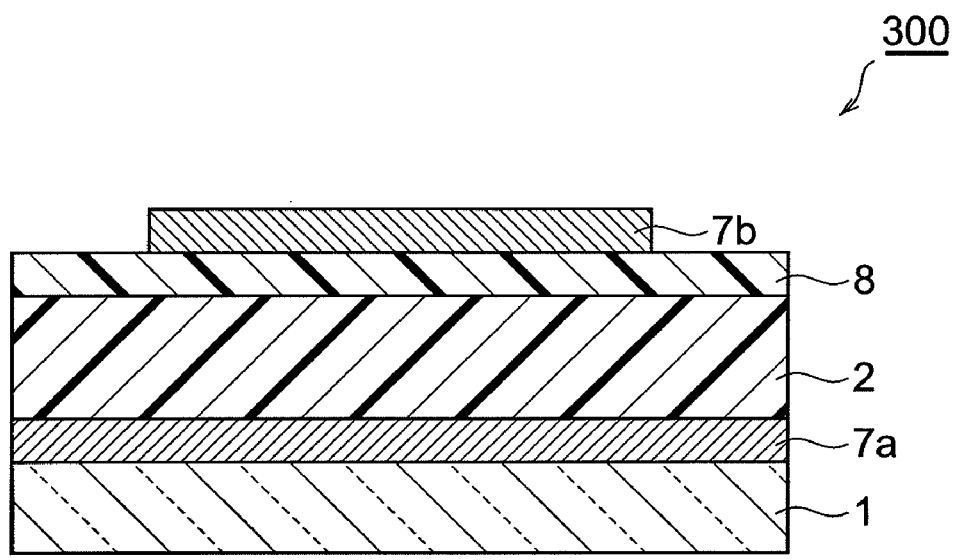
FIG. 6 is a schematic cross-sectional view of an optical sensor according to a first embodiment.

FIG. 6 is a schematic cross-sectional view of an optical sensor according to a first embodiment. The optical sensor 300 shown in FIG. 6 comprises a substrate 1, a first electrode 7a formed on the substrate 1, an active layer 2 comprising an organic thin-film that contains a polymer of the invention formed on the first electrode 7a, a charge generation layer 8 formed on the active layer 2 and a second electrode 7b formed on the charge generation layer 8.

Figure 7:
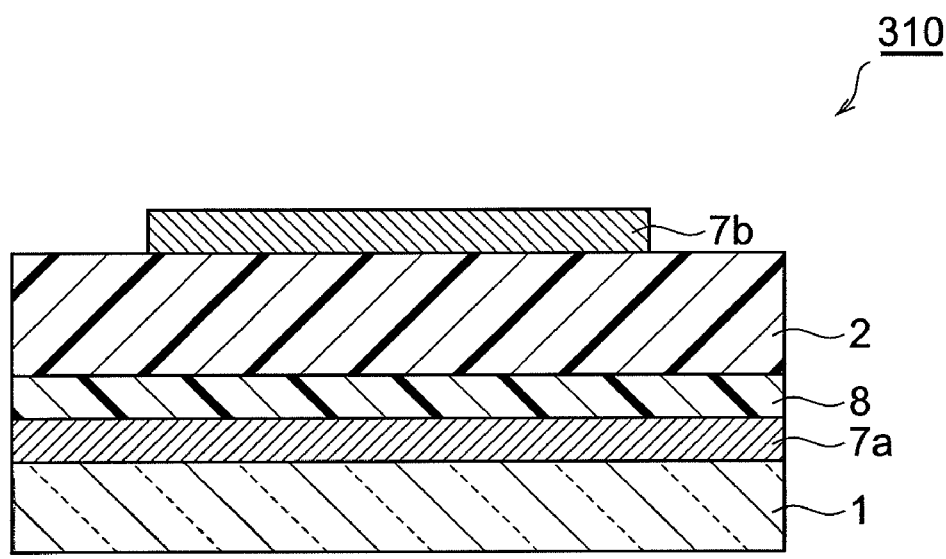
FIG. 7 is a schematic cross-sectional view of an optical sensor according to a second embodiment.

FIG. 7 is a schematic cross-sectional view of an optical sensor according to a second embodiment. The optical sensor 310 shown in FIG. 7 comprises a substrate 1, a first electrode 7a formed on the substrate 1, a charge generation layer 8 formed on the first electrode 7a, an active layer 2 comprising an organic thin-film that contains a polymer of the invention formed on the charge generation layer 8, and a second electrode 7b formed on the active layer 2.

Figure 8:
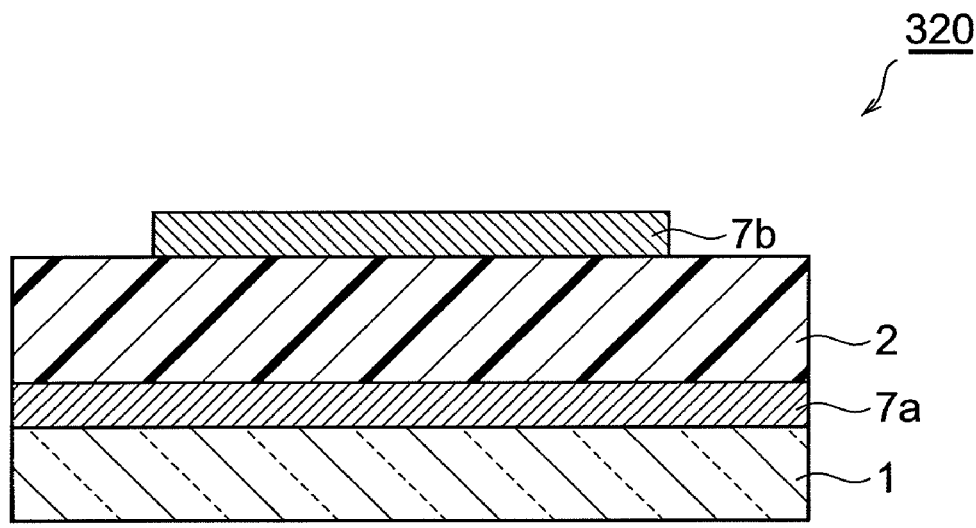
FIG. 8 is a schematic cross-sectional view of an optical sensor according to a third embodiment.

FIG. 8 is a schematic cross-sectional view of an optical sensor according to a third embodiment. The optical sensor 320 shown in FIG. 8 comprises a substrate 1, a first electrode 7a formed on the substrate 1, an active layer 2 comprising an organic thin-film that contains a polymer of the invention formed on the first electrode 7a, and a second electrode 7b formed on the active layer 2.

In the optical sensors of the first to third embodiments, a transparent or semi-transparent electrode is used for either or both the first electrode 7a and second electrode 7b. The charge generation layer 8 is a layer that generates a charge upon absorption of light. As electrode materials there may be used metals such as aluminum, gold, silver, copper, alkali metal and alkaline earth metals or their semi-transparent films, or transparent conductive films. Carrier generators, sensitizing agents and the like may also be added in order to increase photosensitivity in the active layer 2 (organic thin-film). The substrate 1 may be a silicon substrate, glass substrate, plastic substrate or the like.

EXAMPLES

The present invention will now be explained in greater detail based on examples and comparative examples, with the understanding that these examples are in no way limitative on the invention.

(Measuring Conditions)

The nuclear magnetic resonance (NMR) spectrum was measured using a JMN-270™ (270 MHz for $^1$H measurement) or a JMNLA-600™ (600 MHz for $^{19}$F measurement), both by JEOL Corp. The chemical shifts are represented as parts per million (ppm). Tetramethylsilane (TMS) was used as the internal standard (0 ppm). The coupling constant (J) is represented in Hz, and the symbols s, d, t, q, m and br respectively represent singlet, doublet, triplet, quartet, multiplet and broad. The mass spectrometry (MS) was performed using a GCMS-QP5050A™ by Shimadzu Corp., by electron ionization (EI) or direct inlet (DI). The silica gel used for separation by column chromatography was Silicagel™ 60N (40-50 μm) by Kanto Kagaku Co., Ltd. All of the chemical substances were reagent grade and purchased from Wako Pure Chemical Industries, Ltd., Tokyo Kasei Kogyo Co., Ltd., Kanto Kagaku Co., Ltd., Nacalai Tesque, Inc., Sigma Aldrich Japan, KK. or Daikin Chemicals Co., Ltd.

Cyclic voltammetry was performed using an apparatus by BAS, with a Pt electrode by BAS as the work electrode, a Pt wire as the counter electrode and a Ag wire as the reference electrode. The sweep rate during measurement was 100 mV/sec, and the scanning potential range was −2.8 V to 1.6 V. The reduction potential and oxidation potential were measured after completely dissolving $1\times10^{-3}$ mol/L of the compound and 0.1 mol/L of tetrabutylammonium hexafluorophosphate (TBAPF6) as a supporting electrolyte in a monofluorobenzene solvent. X-ray diffraction (XRD) was performed using a Rigaku RAXIS-RAPID imaging plate diffractometer.

Reference Synthesis Example 1

Synthesis of Monomer A

The starting material 1,3-dibromo-cyclopenta[c]thiophene-4,6(5H)-dione (73) was synthesized with reference to Khanh, L. P.; Dallemagne, P.; Rault, S. Synlett, 1999, 9, 1450-1452.

Compound (73) was used as the starting material for synthesis of compounds (74), (75) and (76) by a two-stage fluorination reaction according to the following Scheme 1. Specifically, first an ethyl acetate solution (5 mL) containing [1,3-d]bromo-4H-cyclopenta[c]thiophene-4,6(5H)-dione (1.00 g, 3.25 mmol) and N-fluoro-6-(trifluoromethyl)pyridinium-2-sulfonate (MEC-04B) (1.75 g, 7.14 mmol) was prepared and stirred at 85° C. for 4 hours. The reaction mixture was cooled to room temperature, poured into water and extracted with ethyl acetate. The extracted organic layer was washed with saturated saline and dried over anhydrous sodium sulfate, and after filtering out the insoluble portion, the solvent was distilled off under reduced pressure. The obtained residue was isolated and purified by silica gel column chromatography (hexane/chloroform (1:1)) to obtain compound (74) (1.53 g, 75% yield). Next, a chloroform solution (10 mL) was prepared containing compound (74) (1.53 g, 4.42 mmol), 1,2-ethanedithiol (1.25 g, 13.27 mmol) and boron trifluoride-acetate complex (2.50 g, 13.27 mmol), and the mixture was stirred at 60° C. for 4 hours. The reaction mixture was cooled to room temperature, poured into water and extracted with chloroform. The extracted organic layer was washed with saturated saline and dried over anhydrous sodium sulfate, and after filtering out the insoluble portion, the solvent was distilled off under reduced pressure. The obtained residue was isolated and purified by silica gel column chromatography (hexane/chloroform (1:1)) to obtain compound (75) (1.80 g, 82% yield).

Next, a methylene chloride solution (10 mL) was prepared containing 1,3-dibromo-5,5-dimethylhydantoin (10.32 g, 36.10 mmol) and was cooled to −78° C. There was then added dropwise (HF)$_9$/pyridine (18 mL) while keeping the temperature at −78° C., and the mixture was stirred for 10 minutes. A methylene chloride solution (30 mL) containing compound (75) (1.80 g, 3.61 mmol) was added dropwise while maintaining the temperature, and the mixture was stirred for 3 hours. After then raising the temperature of the reaction system to room temperature, it was further stirred overnight. The obtained reaction mixture was filtered with basic alumina and the filtrate (organic layer) was washed with aqueous sodium hydrogencarbonate and then with saturated saline. The filtrate was dried over anhydrous sodium sulfate, and after filtering out the insoluble portion, the solvent was distilled off under reduced pressure. The obtained residue was isolated and purified by silica gel column chromatography (hexane) to obtain compound (76) (1.80 g, 82% yield). Compound (76) will hereinafter be referred to as monomer A.

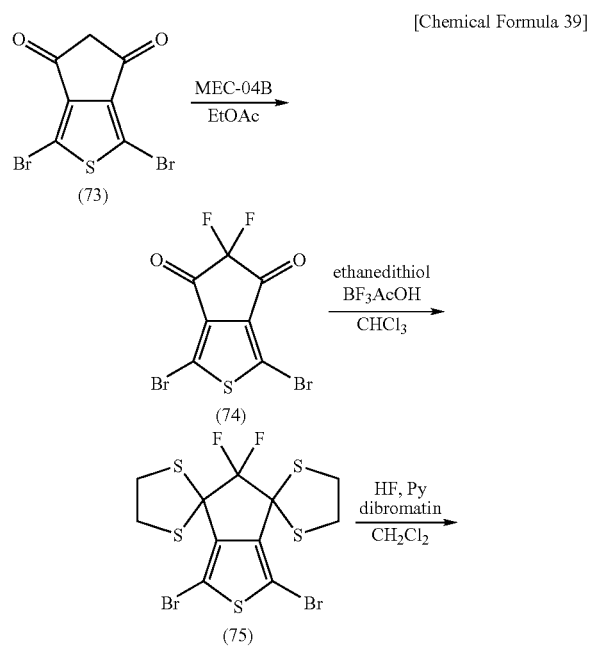

Reference Synthesis Example 2

Synthesis of Monomer B

A THF solution containing a dibromo compound (monomer A) was placed in a heat-dried two-necked volumetric flask under reduced pressure in a nitrogen atmosphere, and n-butyllithium (1.6 M hexane solution) was added at −78° C. After one hour, water was added for quenching and extraction was performed with ether. After drying the organic layer under anhydrous magnesium sulfate, it was filtered and concentrated under reduced pressure and supplied to column chromatography for purification to obtain a monobromo compound (monomer B) as the target compound.

Reference Synthesis Example 3

Synthesis of Monomer C

A monobromo compound (monomer B) (100 mg, 0.353 mmol), hexamethylditin (1.02 g, 1.765 mmol) and tetrakis(triphenylphosphine)palladium(0) (20 mg, 0.017 mmol) were placed in a heat-dried stoppered test tube and toluene (2 mL) was added. Following reaction at 120° C., the mixture was allowed to cool and filtered with Celite. Purification was performed by column chromatography (alumina) to obtain a trimethyltin compound (54 mg, 0.103 mmol) (monomer C).

[Chemical Formula 40]

Example 1

Synthesis of Compound A

A dibromo compound (monomer A) (100 mg, 0.257 mmol), 2-tributylstannylthiophene (290 mg, 0.732 mmol) and tetrakis(triphenylphosphine)palladium(0) (30 mg, 0.026 mmol) were placed in a heat-dried stoppered test tube. After adding toluene (1 mL), the mixture was bubbled with nitrogen and reaction was conducted at 120° C. When 12 hours had passed, it was allowed to stand, filtered with Celite and then concentrated under reduced pressure. Finally it was purified by column chromatography (silica gel, hexane charge) hexane:CH$_2$Cl$_2$=10:1 to obtain the target substance (94 mg, 91%) as a light yellow solid (compound A).

TLC R$_f$=0.45 (hexane): $^1$H-NMR (270 MHz, CDCl$_3$) δ 7.13 (dd, 2H, J=4.6, 3.6 Hz), 7.43-7.45 (m, 4H): MS (EI) m/z 396 (M$^+$).

[Chemical Formula 41]

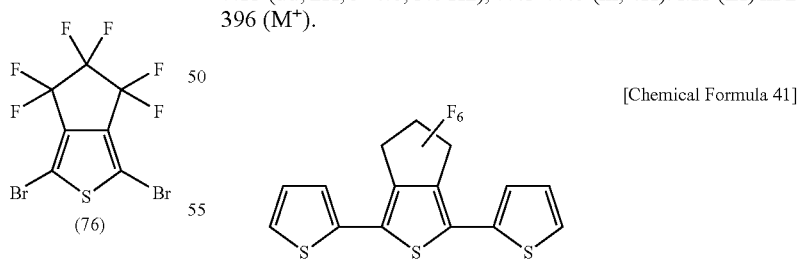

Example 2

Synthesis of Compound B

Compound A (216 mg, 0.545 mmol) was placed in a 100 mL volumetric flask and dissolved in carbon tetrachloride (9 mL), and then bistrifluoroacetic acid/iodobenzene (117 mg, 0.272 mmol) and iodine (69 mg, 0.272 mmol) were added at 0° C. After 2 hours, saturated aqueous sodium thiosulfate was added for quenching and extraction was performed with chloroform. The mixture was washed with water, and after drying the organic layer over anhydrous magnesium sulfate, it was filtered and concentrated under reduced pressure. It was then supplied to hexane in column chromatography (silica gel, hexane charge) for purification to obtain the target substance (174 mg, 61%) as a yellow solid (compound B).

TLC $R_f$=0.51 (hexane): MS (DI) m/z 522 (M$^+$): $^1$H-NMR (270 MHz, CDCl$_3$) δ 7.13 (t, 1H, J=4.4 Hz), 7.15 (d, 1H, J=3.3 Hz), 7.43 (d, 2H, J=4.4 Hz), 7.54 (d, 1H, J=3.3 Hz).

[Chemical Formula 42]

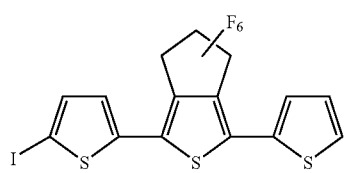

Example 3

Synthesis of Compound C

A dibromo compound (monomer A) (500 mg, 1.28 mmol), 2-tributylstannyl-5-perfluorohexylthiophene (887 mg, 1.28 mmol), 2-tributylstannylthiophene (994 mg, 3.84 mmol) and tetrakis(triphenylphosphine)palladium(0) (148 mg, 0.128 mmol) were placed in a heat-dried stoppered test tube. After adding toluene (10 mL), the mixture was bubbled with nitrogen and reacted at 120° C. When 12 hours had passed, it was allowed to stand, filtered with Celite and then concentrated under reduced pressure. Finally, it was purified by GPC (CHCl$_3$) to obtain the target substance (399 mg, 44%) as a light yellow solid (compound C).

TLC $R_f$=0.50 (hexane): $^1$H-NMR (270 MHz, CDCl$_3$) δ 7.13-7.17 (m, 1H), 7.42-7.50 (m, 4H): MS (DI) m/z 714 (M$^+$).

[Chemical Formula 43]

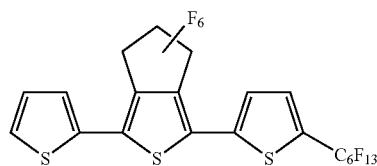

Example 4

Synthesis of Compound D

Compound C (538 mg, 0.753 mmol) was placed in a 100 mL volumetric flask and dissolved in carbon tetrachloride (8 mL), and then bistrifluoroacetic acid/iodobenzene (162 mg, 0.376 mmol) and iodine (96 mg, 0.376 mmol) were added at 0° C. After 2 hours, saturated aqueous sodium thiosulfate was added for quenching and extraction was performed with chloroform. The mixture was washed with water, and after drying the organic layer over anhydrous magnesium sulfate, it was filtered and concentrated under reduced pressure. It was then supplied to hexane in column chromatography (silica gel, hexane charge) for purification to obtain the target substance (619 mg, 98%) as a yellow solid (compound D).

$^1$H-NMR (270 MHz, CDCl$_3$) δ 7.12 (d, 1H, J=4.0 Hz), 7.30 (d, 1H, J=4.0 Hz), 7.43-7.45 (m, 2H).

[Chemical Formula 44]

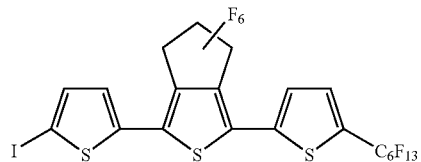

Example 5

Synthesis of Oligomer B

A dibromo compound (monomer A) (100 mg, 0.257 mmol), 2-tributylstannyl-5-perfluorohexylthiophene (533 mg, 0.770 mmol) and tetrakis(triphenylphosphine)palladium (0) (30 mg, 0.026 mmol) were placed in a heat-dried stoppered test tube. After adding toluene (1 mL), the mixture was bubbled with nitrogen and reacted at 120° C. When 12 hours had passed, it was allowed to stand, filtered with Celite and then concentrated under reduced pressure. It was then supplied to hexane in column chromatography (silica gel, hexane charge) for purification to obtain the target substance (214 mg, 81%) as a light yellow solid (oligomer B).

mp 69-71° C.: TLC $R_f$=0.54 (hexane): $^1$H-NMR (270 MHz, acetone-d$_6$) δ 7.75-7.77 (m, 1H), 7.83 (1H, d, J=4.0 Hz): MALDI TOF-MS m/z 1037.57 (M+, Calcd 1031.90)

[Chemical Formula 45]

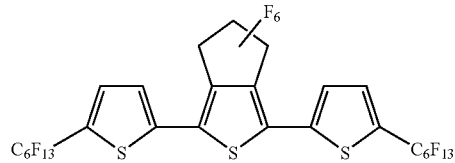

Example 6

Synthesis of Oligomer C

A dibromo compound (monomer A) (100 mg, 0.255 mmol), 5,5'-bistributylstannyl-2,2'-bithiophene (44 mg, 0.085 mmol) and tetrakis(triphenylphosphine)palladium(0) (10 mg, 8.5 μmol) were placed in a heat-dried stoppered test tube. After adding toluene (1 mL), the mixture was bubbled with nitrogen and reacted at 120° C. When 16 hours had passed, it was allowed to stand, filtered with Celite and then concentrated under reduced pressure. Finally, it was purified by preparative column chromatography (CHCl$_3$) hexane: CHCl$_3$=4:1 to obtain the target substance (20 mg, 30%) as a yellow solid (oligomer C).

TLC $R_f$=0.66 (4:1 hexane/CHCl$_3$): $^1$H-NMR (270 MHz, CD$_2$Cl$_2$) δ 7.20 (d, 2H, J=4.0 Hz), 7.27 (d, 2H, J=4.0 Hz): MS (MALDI-TOF, 1,8,9-trihydroxyanthracene matrix) m/z 788.8 (M$^+$, Calcd 784.3).

[Chemical Formula 46]

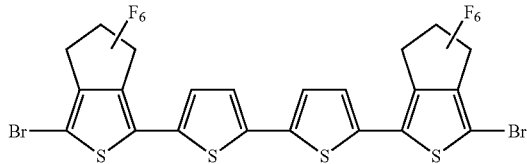

Example 7

Synthesis of Oligomer D

Compound D (77 mg, 0.092 mmol), palladium acetate(II) (21 mg, 0.092 mmol) and diisopropylamine (56 mg, 0.553 mmol) were placed in a heat-dried stoppered test tube. After dissolving this mixture in toluene (1.5 mL), it was bubbled with nitrogen and reacted at 120° C. When 12 hours had passed, it was allowed to stand, filtered with Celite and then concentrated under reduced pressure. Finally, it was supplied to hexane:ethyl acetate=1:0-10:1-5:1-3:1 in column chromatography (silica gel, CHCl$_3$ charge) for purification to obtain the target substance (14 mg, 21%) as a reddish-orange solid (oligomer D).

TLC R$_f$=0.69 (4:1 hexane/CHCl$_3$): $^1$H-NMR (270 MHz, CDCl$_3$) δ 7.13-7.18 (m, 4H), 7.49-7.53 (m, 4H): MS (MALDI-TOF, 1,8,9-trihydroxyanthracene matrix) m/z 1434.2 (M$^+$, Calcd 1426.8).

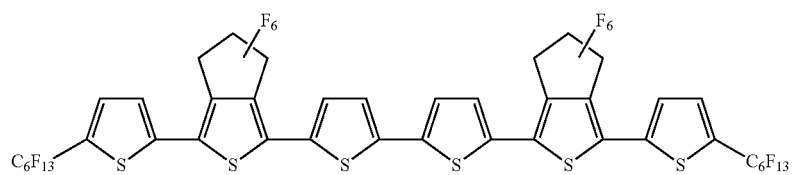

Example 8

Synthesis of Oligomer E

Compound B (51 mg, 0.098 mmol), palladium acetate (II) (22 mg, 0.098 mmol) and diisopropylamine (59 mg, 0.588 mmol) were placed in a heat-dried stoppered test tube. After dissolving this mixture in toluene (1.5 mL), it was bubbled with nitrogen and reacted at 120° C. When 12 hours had passed, it was allowed to stand, filtered with Celite and then concentrated under reduced pressure. Finally, it was supplied to hexane:ethyl acetate=1:0-10:1-5:1-3:1 in column chromatography (silica gel, CHCl$_3$ charge) for purification to obtain the target substance (12 mg, 31%) as a reddish-orange solid (oligomer E).

TLC R$_f$=0.34 (5:1 hexane/CH$_2$Cl$_2$): $^1$H-NMR (270 MHz, THF-d8) δ 8.96-9.01 (m, 2H), 9.27-9.35 (m, 6H), 9.47-9.52 (m, 2H): MS (DI) m/z 790 (M$^+$).

[Chemical Formula 48]

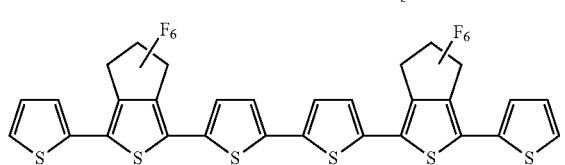

Example 9

Synthesis of Oligomer F

A THF solution (1 mL) containing a dibromo compound (monomer A) (110 mg, 0.282 mmol) was placed in a heat-dried two-necked volumetric flask under reduced pressure in a nitrogen atmosphere, and then n-butyllithium (1.6 M hexane solution, 0.19 mL, 0.311 mmol) was added at −78° C. After one hour, copper bromide (II) (126 mg, 0.564 mmol) was added, the mixture was stirred at −78° C. for 30 minutes and the temperature was raised to room temperature. After 2.5 hours, water (20 mL) was added for quenching and filtration was performed with Celite. Extraction was then performed with CHCl$_3$ (20 mL×2) and the organic layer was dried over anhydrous magnesium sulfate, filtered and concentrated under reduced pressure. Column chromatography (silica gel, CHCl$_3$ charge) was then performed for purification with the solvent mixing ratio changed to hexane:CHCl$_3$=1:0-10:1-5:1-3:1 to obtain the target substance (57 mg, 65%) as a yellow solid (oligomer F).

TLC R$_f$=0.49 (4:1 hexane/CHCl$_3$): MS (DI) m/z 620 (M$^+$).

[Chemical Formula 49]

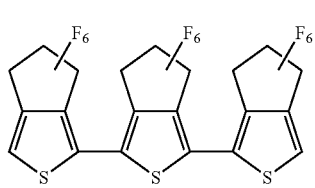

[Chemical Formula 47]

Example 10

Synthesis of Oligomer G

A dibromo compound (monomer A) (18 mg, 0.047 mmol), a trimethyltin compound (monomer C) (54 mg, 0.103 mmol) and tetrakis(triphenylphosphine)palladium(0) (5 mg, 4.0 μmol) were placed in a heat-dried stoppered test tube. After adding toluene (1 mL), the mixture was bubbled with nitrogen for reaction at 120° C. When 16 hours had passed, it was allowed to stand, filtered with Celite and then concentrated under reduced pressure. Finally, it was purified by preparative column chromatography (CHCl$_3$) hexane:CHCl$_3$=10:1 to obtain the target substance (10 mg, 32%) as a yellow solid (oligomer G).

$^1$H-NMR (270 MHz, CDCl$_3$) δ 8.03 (s, 2H): MS (DI) m/z 692 (M$^+$)

[Chemical Formula 50]

Example 11

Synthesis of Oligomer L

A THF solution containing oligomer F is placed in a heat-dried two-necked volumetric flask under reduced pressure in a nitrogen atmosphere, and n-butyllithium (1.6 M hexane solution) is added at 78° C. After one hour, copper (II) bromide is added and the mixture is stirred overnight. Water is added for quenching and extraction is performed with ethyl acetate. The organic layer is dried over anhydrous magnesium sulfate, filtered and concentrated under reduced pressure. It is then purified by column chromatography and supplied to GPC(CHCl$_3$) to obtain the target substance (oligomer L).

[Chemical Formula 51]

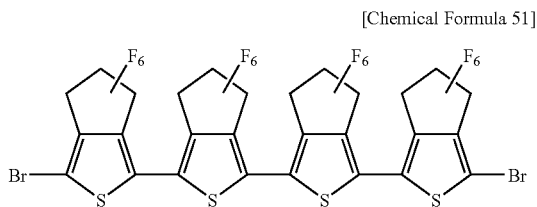

Example 12

Synthesis of Oligomer I

The aforementioned dibromo compound (oligomer L), monomer C synthesized in Reference Synthesis Example 3 and tetrakis(triphenylphosphine)palladium(0) were placed in a heat-dried stoppered test tube. After adding toluene and reacting at 120° C., the mixture was allowed to cool and filtered with Celite. It is then purified by column chromatography (alumina) to obtain the target substance (oligomer I).

[Chemical Formula 52]

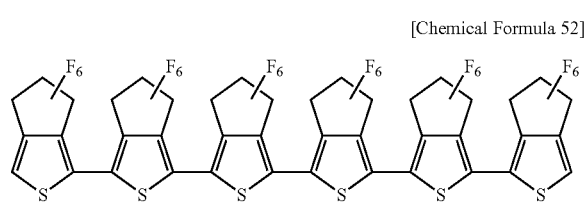

Example 13

Fabrication of Organic Thin-Film Element and Evaluation of Organic Thin-Film Transistor Property A silicon oxide film as the insulating layer was formed by thermal oxidation to a thickness of 300 nm on the surface of a highly doped n-type silicon substrate as the gate electrode. The lift-off method was used to form on this substrate a comb-shaped source electrode and drain electrode with a channel width of 38 mm and a channel length of 5 μm. The electrode-formed substrate was subjected to ultrasonic cleaning for 10 minutes in acetone and for 10 minutes in isopropyl alcohol, after which it was irradiated with ozone UV for 30 minutes to clean the surface. The cleaned substrate was then further surface treated using hexamethyldisilazane (HMDS, product of Aldrich Co.). Oligomer D was accumulated on the substrate to 50 nm by vacuum vapor deposition at a degree of vacuum of about 10$^{-5}$ Pa, a substrate temperature of 100° C. and a deposition rate of 0.002 nm/s, to fabricate an organic thin-film element. The organic thin-film transistor characteristic was measured by varying the gate voltage Vg from 0 to +60 V and the source-drain voltage Vsd from 0 to +50 V for the fabricated organic thin-film element in a vacuum, and a satisfactory n-type semiconductor Id-Vg characteristic was obtained. The drain current Id was 7 nA with application of Vg=60 V, Vsd=30 V.

Example 14

Synthesis of Oligomer J

A THF solution (2 mL) containing oligomer F (123 mg, 0.198 mmol) was placed in a heat-dried two-necked volumetric flask under reduced pressure in a nitrogen atmosphere, and then lithium aluminum hydride (45 mL, 1.188 mmol) was added at 0° C. After 2 hours, water and aqueous 2N sodium hydroxide were added for quenching, and the mixture was filtered with Celite. It was then extracted with ethyl acetate, and the organic layer was dried over anhydrous magnesium sulfate, filtered and concentrated under reduced pressure. Finally, it was supplied to hexane:ethyl acetate=1:0-10:1-5:1-3:1 in column chromatography (silica gel, CHCl$_3$ charge) for purification to obtain the target substance (73 mg, 80%) as a white solid (oligomer J).

TLC R$_f$=0.61 (4:1 hexane/ethyl acetate): $^1$H-NMR (270 MHz, CDCl$_3$) δ 7.97 (s, 2H): MS (EI) m/z 462 (M$^+$).

[Chemical Formula 53]

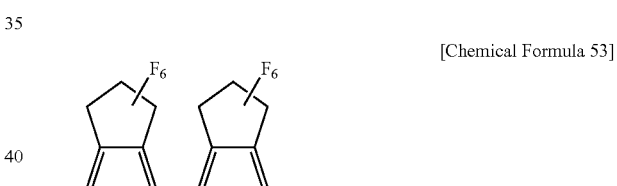

Example 15

Synthesis of Oligomer K

A THF solution (2 mL) containing oligomer J (87 mg, 0.189 mmol) was placed in a heat-dried two-necked volumetric flask under reduced pressure in a nitrogen atmosphere, and then n-butyllithium (1.6 M hexane solution, 0.11 mL, 0.189 mmol) was added at −78° C. After one hour, copper(II) bromide (84 mg, 0.376 mmol) was added and the mixture was stirred overnight. Water was added for quenching and extraction was performed with ethyl acetate. The organic layer was dried over anhydrous magnesium sulfate, filtered and concentrated under reduced pressure. Finally, it was purified by column chromatography and supplied to GPC(CHCl$_3$) to obtain the target substance (5 mg, 6%) as a yellow solid (oligomer K).

TLC R$_f$=0.45 (4:1 hexane/ethyl acetate): $^1$H-NMR (270 MHz, CDCl$_3$) δ 8.07 (s, 2H): MS (MALDI-TOF, 1,8,9-trihydroxyanthracene matrix) m/z 911.2 (M$^+$, 921.9 Calcd).

[Chemical Formula 54]

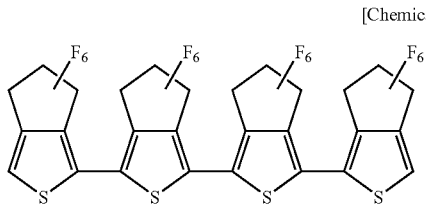

Example 16

Synthesis of Oligomer M

A THF solution containing compound A is placed in a heat-dried two-necked volumetric flask under reduced pressure in a nitrogen atmosphere, and n-butyllithium (1.6 M hexane solution) is added at −78° C. After one hour, tributyltin chloride is added, the mixture is stirred at −78° C. for 30 minutes and the temperature was raised to room temperature. After adding water for quenching and performing extraction with $CHCl_3$, the organic layer is dried over anhydrous magnesium sulfate, filtered, concentrated under reduced pressure and supplied to column chromatography ($Al_2O_3$) for purification to obtain the tributyltin derivative of compound A (compound E).

[Chemical Formula 55]

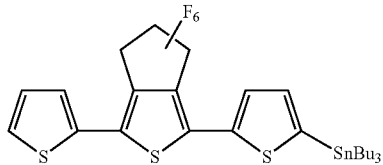

The tributyltin compound (compound E), monomer A and tetrakis(triphenylphosphine)palladium(0) are placed in a heat-dried stoppered test tube. After adding toluene and conducting reaction at 120° C., the mixture is allowed to cool and purified by column chromatography to obtain the target compound (oligomer M).

[Chemical Formula 56]

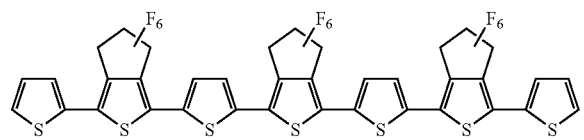

Example 17

Synthesis of Oligomer N

Oligomer F, 5-(tributylstannyl)-5'-(1-perfluorohexyl)-2,2'-bithiophene and tetrakis(triphenylphosphine)palladium(0) are placed in a heat-dried stoppered test tube. After adding toluene and conducting reaction at 120° C., the mixture is allowed to cool and purified by column chromatography to obtain the target compound (oligomer N).

[Chemical Formula 57]

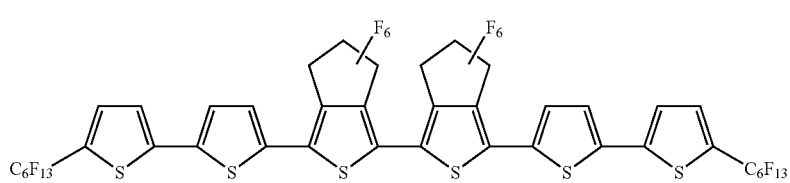

Example 18

Oligomer E was used for X-ray structural analysis, and the dihedral angle between adjacent thiophene rings was measured to be approximately 20 degrees. This value is smaller than the dihedral angle of 45.6 degrees for an oligothiophene with fluoroalkyl groups introduced onto side chains (general formula (A) below) as described in the literature (J. Am. Chem. Soc., 126 (2004) 13480), and indicates that oligomer E has a high degree of planarity.

[Chemical Formula 58]

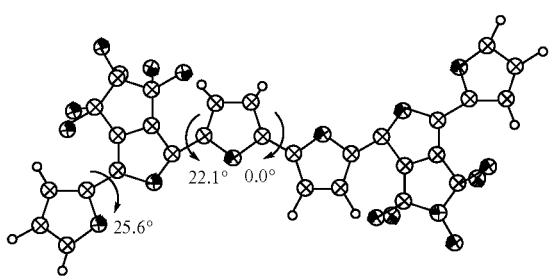

[Chemical Formula 59]

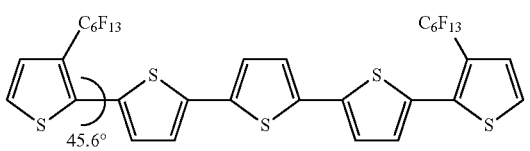

(A)

Reference Synthesis Example 4

Synthesis of Monomer D

First, 2,7-dibromo-9,9-dioctylfluorene (5.00 g, 9.12 mmol) was placed in a 500 mL four-necked flask under an argon stream. After then adding toluene (100 mL), the mixture was cooled to −78° C. in an acetone bath. Sec-butyllithium (19.86 mL, 2.01 mmol) was slowly added dropwise to the mixture without allowing the temperature of the system to rise above −70° C. Upon completion of the dropwise addition, the reaction mixture was stirred at −78° C. for 2 hours and a solution of trimethylstannyl chloride (4.00 g, 2.01 mmol) in THF (50 mL) was then added dropwise over a period of 20 minutes. Stirring was continued at −78° C. for 2 hours. After then raising the temperature of the reaction system to room temperature, it was further stirred overnight. Upon completion of the reaction, the mixture was poured into 500 mL of water and extracted 5 times with methylene chloride (50 mL). The extracted organic layer was washed with saturated saline and then with water. The organic layer was dried over magnesium sulfate, and after filtering out the insoluble matter, the solvent was distilled off under reduced pressure to obtain a brown oily residue. The obtained residue was isolated by reverse-phase column chromatography (developing solvent: acetonitrile) and recrystallized from ethanol to obtain 2,7-bis(trimethylstannyl)-9,9-dioctylfluorene (2.82 g, 3.93 mmol, 43% yield) (monomer D) as colorless crystals.

[Chemical Formula 60]

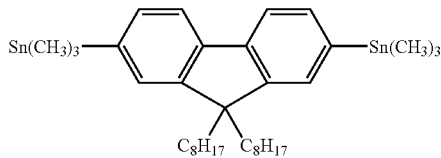

Example 19

Synthesis of Polymer A

In a 50 mL carousel test tube there were placed monomer A (50 mg, 0.128 mmol), monomer D (230 mg, 0.321 mmol), 2,7-dibromo-9,9-dioctylfluorene (105 mg, 0.192 mmol), tris(dibenzylideneacetone)dipalladium (5.87 mg, 0.006 mmol) and tri(o-tolyl)phosphine (3.90 mg, 0.013 mmol), under an argon stream. After adding chlorobenzene (5 mL) to the mixture, reaction was conducted at 105° C. After 8 hours the mixture was allowed to cool and then poured into a methanol (50 mL)/37% concentrated hydrochloric acid (5 mL) mixture and stirred for 30 minutes. The deposited polymer was filtered with a Kiriyama funnel and washed with methanol and acetone to obtain the target substance (150 mg) as a light yellow solid (polymer A). The polystyrene-based number-average molecular weight of the obtained polymer A was $4.8 \times 10^3$.

$^{19}$F-NMR (280 MHz, CDCl$_3$-CFCl$_3$) δ 106.2 (m), δ 126.6 (m)

[Chemical Formula 61]

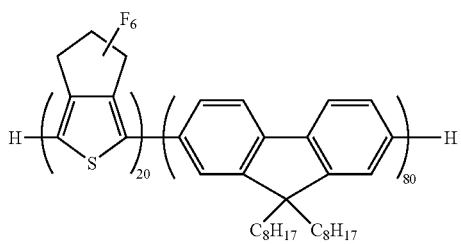

The reduction potentials of compound A and oligomers B, D, E, G and K were measured by the method described above under "Measuring Conditions". The results are shown in Table 1.

TABLE 1

| Oligomer | Reduction potential (V) |
|---|---|
| Compound A | −1.93 |
| Oligomer B | −1.57 |
| Oligomer D | −1.55 |
| Oligomer E | −1.55 |
| Oligomer G | −1.51 |
| Oligomer K | −1.27 |

A comparison of compound A with oligomer E shows that the reduction potential of the hexamer was lower (smaller absolute value) than that of the trimer. Also, a comparison of oligomer G with oligomer K shows that the reduction potential of the tetramer was lower (smaller absolute value) than that of the trimer. Thus, the LUMO is sufficiently reduced and a satisfactory electron transport property is obtained with tetramers and higher oligomers.

INDUSTRIAL APPLICABILITY

The invention provides novel polymers that can be used as organic n-type semiconductors with excellent electron transport properties. The invention further provides organic thin-films containing the novel polymers and organic thin-film elements comprising the organic thin-films. Among the novel polymers, those with a 3,3,4,4,5,5-hexafluorocyclopenta[c]thiophene structure have a particularly low LUMO level due to introduction of the fluorocyclopentane ring, and their solubility in organic solvents is increased while π conjugated planarity is maintained. The novel polymers are therefore useful as organic n-type semiconductors with exceptionally high electron transport properties. The novel polymers can also be easily obtained by oligomerization or polymerization of starting compounds. The polymers of the invention obtained in this manner are especially useful for production of organic transistors, organic solar cells, optical sensors and the like.

The invention claimed is:
1. A polymer comprising a repeating unit represented by the following general formula (II)

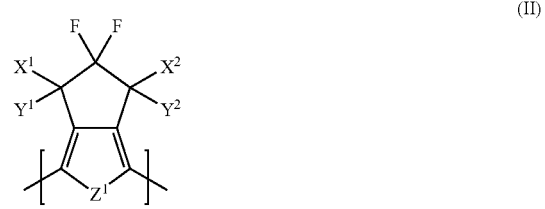

wherein $X^1$, $Y^1$, $X^2$ and $Y^2$ each independently represent a fluorine atom or alkylthio group (with $X^1$ and $Y^1$ optionally having their alkyl portions linked to form an alkylenedithio group, and $X^2$ and $Y^2$ optionally having their alkyl portions linked to form an alkylenedithio group),
with the proviso that $X^1$ and $Y^1$ may together form a carbonyl or thiocarbonyl group with their bonding carbon atom, and $X^2$ and $Y^2$ may together form a carbonyl or thiocarbonyl group with their bonding carbon atom, and $Z^1$ is a group represented by any of the following formulas (i)-(ix), with the proviso that $R^1$, $R^2$, $R^3$ and $R^4$ each independently represent hydrogen or a substituent

 (i)

 (ii)

 (iii)

 (iv)

 (v)

 (vi)

 (vii)

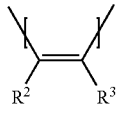 (viii)

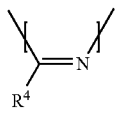 (ix)

2. A polymer according to claim 1, which comprises at least one repeating unit represented by general formula (II) and at least one repeating unit represented by the following general formula (III) which is different from the repeating unit represented by general formula (II)

 (III)

wherein $Ar^2$ represents a divalent aromatic hydrocarbon or divalent heterocyclic group (which may be optionally substituted).

3. A polymer according to claim 2, wherein $Ar^2$ is a group represented by the following formula (IV)

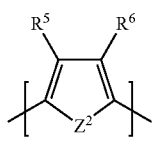 (IV)

wherein $Z^2$ is a group represented by any of the following formulas (i)-(ix), $R^1$, $R^2$, $R^3$ and $R^4$ each independently represent hydrogen or a substituent, $R^5$ and $R^6$ each independently represent hydrogen or a substituent and $R^5$ and $R^6$ may optionally form a ring

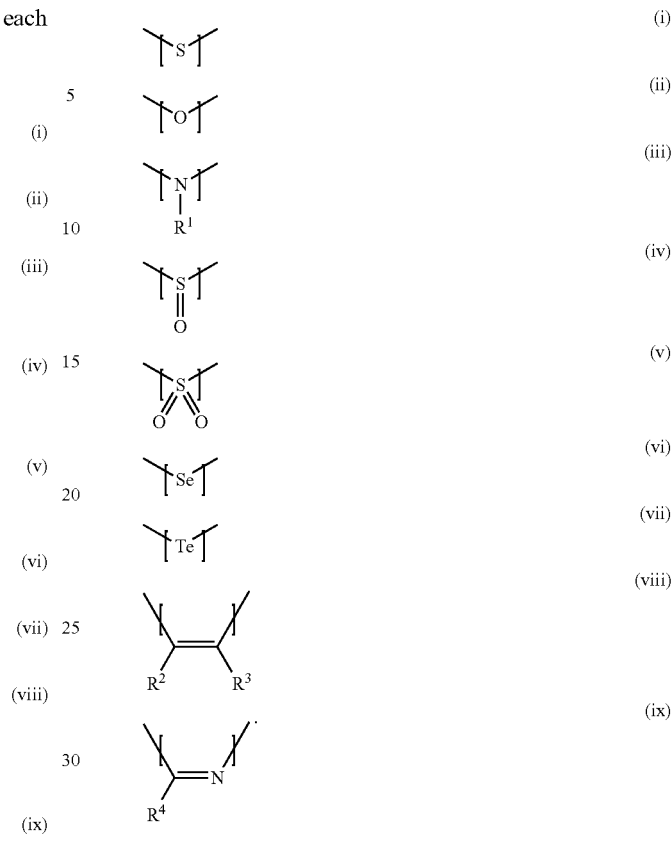

4. A polymer according to claim 1, which comprises at least four repeating units represented by general formula (II).

5. A polymer according to claim 1, wherein $R^1$, $R^2$, $R^3$ and $R^4$ each independently represent hydrogen, a halogen atom, a C3-60 monovalent cyclic group (which may be a monocycle or fused ring, a carbon ring or heterocyclic ring, saturated or unsaturated, and with or without substituents), a saturated or unsaturated hydrocarbon group, hydroxyl, alkoxy, alkanoyloxy, amino, oxyamino, alkylamino, dialkylamino, alkanoylamino, cyano, nitro, sulfo, alkyl substituted with one or more halogen atoms, alkoxysulfonyl (optionally substituted with one or more halogen atoms), alkylsulfonyl (optionally substituted with one or more halogen atoms), sulfamoyl, alkylsulfamoyl, carboxyl, carbamoyl, alkylcarbamoyl, alkanoyl or alkoxycarbonyl.

6. A polymer according to claim 3, wherein $R^5$ and $R^6$ each independently represent hydrogen, a halogen atom, a C3-60 monovalent cyclic group (which may be a monocycle or fused ring, a carbon ring or heterocyclic ring, saturated or unsaturated, and with or without substituents), a saturated or unsaturated hydrocarbon group, hydroxyl, alkoxy, alkanoyloxy, amino, oxyamino, alkylamino, dialkylamino, alkanoylamino, cyano, nitro, sulfo, alkyl substituted with one or more halogen atoms, alkoxysulfonyl (where the alkyl group is optionally substituted with one or more halogen atoms), alkylsulfonyl (where the alkyl group is optionally substituted with one or more halogen atoms), sulfamoyl, alkylsulfamoyl, carboxyl, carbamoyl, alkylcarbamoyl, alkanoyl or alkoxycarbonyl.

7. A polymer according to claim 1, wherein $Z^1$ is a group represented by any one of formulas (i), (ii), (iii), (viii) and (ix).

8. A polymer according to claim 1, wherein $Z^1$ is a group represented by formula (i).

9. A polymer according to claim 3, wherein $Z^2$ is a group represented by any one of formulas (i), (ii), (iii), (viii) and (ix).

10. A polymer according to claim 3, wherein $Z^2$ is a group represented by formula (i).

11. A polymer according to claim 1, wherein $X^1, Y^1, X^2$ and $Y^2$ are all fluorine atoms.

12. A polymer according to claim 1, which is represented by any one of the following general formulas (V)-(VII)

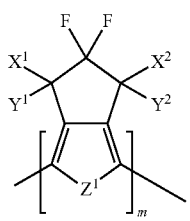
(V)

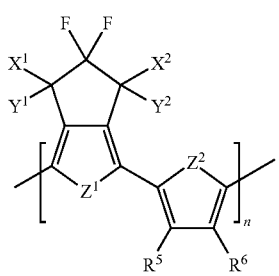
(VI)

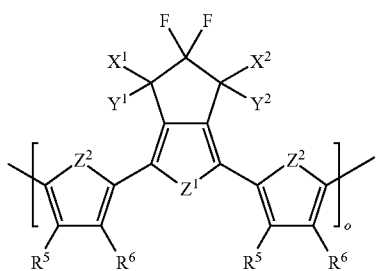
(VII)

wherein $Z^1$ and $Z^2$ each independently represent a group represented by any of the following formulas (i)-(ix), where $R^1$, $R^2$, $R^3$ and $R^4$ each independently represent hydrogen or a substituent, and $X^1, Y^1, X^2$ and $Y^2$ each independently represent a fluorine atom or alkylthio group (with $X^1$ and $Y^1$ optionally bonding at their alkyl portions to form an alkylene-dithio group and $X^2$ and $Y^2$ optionally bonding at their alkyl portions to form an alkylenedithio group), with the proviso that $X^1$ and $Y^1$ may together form a carbonyl or thiocarbonyl group with their bonding carbon atom, and $X^2$ and $Y^2$ may together form a carbonyl or thiocarbonyl group with their bonding carbon atom, $R^5$ and $R^6$ each independently represent hydrogen or a substituent and a ring may be formed between $R^5$ and $R^6$, when a plurality of $Z^1, Z^2, Y^1, X^2, Y^2, R^5$ and $R^6$ are present, they may be either the same or different, and m represents an integer of 2-500, n represents an integer of 1-500 and o represents an integer of 1-500

(i)

(ii)

(iii)

(iv)

(v)

(vi)

(vii)

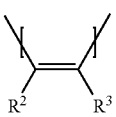
(viii)

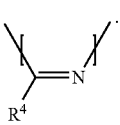
(ix)

13. A polymer according to claim 1, which is represented by any one of the following general formulas (86)-(90)

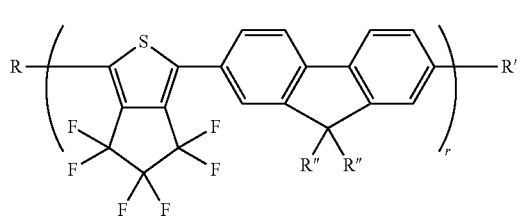
(86)

-continued

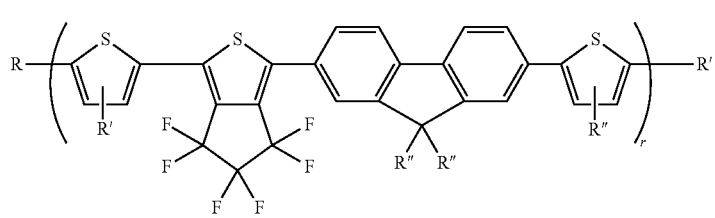 (87)

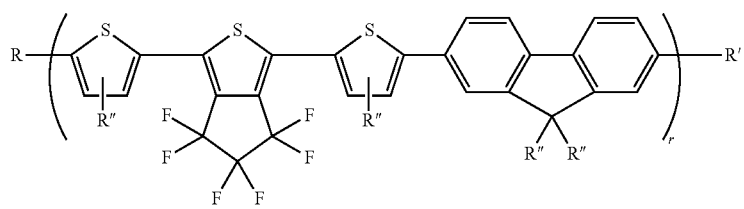 (88)

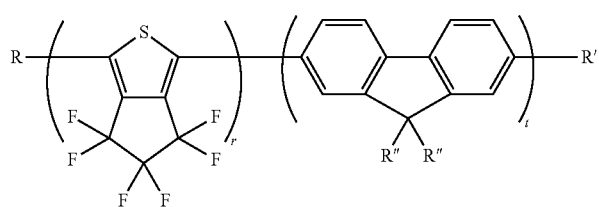 (89)

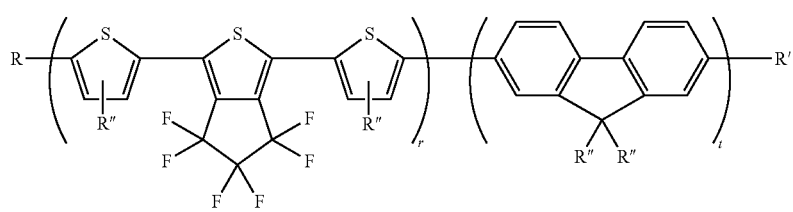 (90)

wherein R and R' represent the same or different terminal groups, each R" independently represents hydrogen or any desired substituent, and r and t each represent an integer of 1-500.

14. An organic thin-film comprising a polymer according to claim 1 and having a film thickness of 1 nm-100 μm.

15. An organic thin-film according to claim 14, which is formed by vacuum vapor deposition, spin coating, ink jet printing, dispenser printing or flexographic printing.

16. An organic thin-film element comprising an organic thin-film according to claim 14.

17. An organic thin-film transistor comprising a source electrode and drain electrode, an organic semiconductor layer serving as a current channel between the electrodes and a gate electrode that controls the level of current flowing through the current channel, wherein the organic semiconductor layer comprises an organic thin-film according to claim 14.

18. An organic solar cell comprising an organic thin-film according to claim 14.

19. An optical sensor comprising an organic thin-film according to claim 14.

* * * * *